United States Patent
Ono et al.

(10) Patent No.: US 12,171,669 B2
(45) Date of Patent: Dec. 24, 2024

(54) SYSTEMS AND METHODS FOR FILLING MATERIAL

(71) Applicant: Spinal Elements, Inc., Carlsbad, CA (US)

(72) Inventors: Matthew Ono, San Diego, CA (US); Marc Yap, Carlsbad, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 558 days.

(21) Appl. No.: 17/493,133

(22) Filed: Oct. 4, 2021

(65) Prior Publication Data

US 2022/0110758 A1    Apr. 14, 2022

Related U.S. Application Data

(60) Provisional application No. 63/090,072, filed on Oct. 9, 2020.

(51) Int. Cl.
| | | |
|---|---|---|
| *A61F 2/46* | (2006.01) | |
| *A61F 2/44* | (2006.01) | |
| *A61F 2/30* | (2006.01) | |

(52) U.S. Cl.
CPC ............. *A61F 2/441* (2013.01); *A61F 2/442* (2013.01); *A61F 2/4455* (2013.01); *A61F 2002/30581* (2013.01)

(58) Field of Classification Search
CPC .......... A61F 2/441; A61F 2/4455; A61F 2/46; B65B 1/10; B65B 1/12

(Continued)

(56) References Cited

U.S. PATENT DOCUMENTS

| | | |
|---|---|---|
| 346,265 A | 7/1886 | Charlton et al. |
| 3,244,271 A | 4/1966 | Wenning |

(Continued)

FOREIGN PATENT DOCUMENTS

| | | |
|---|---|---|
| EP | 2 462 885 | 4/2013 |
| EP | 1 898 809 | 8/2015 |

(Continued)

OTHER PUBLICATIONS

International Search Report and Written Opinion in International Application No. PCT/US2021/071691, dated Dec. 30, 2021.

(Continued)

*Primary Examiner* — Eduardo C Robert
*Assistant Examiner* — Christina Negrelli-Rodriguez
(74) *Attorney, Agent, or Firm* — Knobbe, Martens, Olson & Bear, LLP

(57) ABSTRACT

Various embodiments of filling assemblies and methods are provided. The filling assembly can include a barrel and receiving block assembly configured to couple to a tube. The filling assembly can include a filling auger, wherein the filling auger is configured to rotate and translate to fill the tube with material. The method of filling a tube can include disposing flights of a filling auger within a barrel and receiving block assembly. The method can include coupling a tube to the barrel and receiving block assembly. The method can include rotating and translating flights of the filling auger within the barrel and receiving block assembly to fill the tube with material. The filling assemblies can be utilized for loading material into small diameter tubes, including small diameter tubes used for spinal fusion for delivering graft material, biologics, and/or other material to the disc space.

20 Claims, 20 Drawing Sheets

(58) Field of Classification Search
USPC .................................................. 606/92, 93
See application file for complete search history.

(56) References Cited

U.S. PATENT DOCUMENTS

| | | | |
|---|---|---|---|
| 4,065,034 A | 12/1977 | Callan | |
| 4,443,149 A | 4/1984 | Isaacson | |
| 4,594,073 A | 6/1986 | Stine | |
| 5,071,040 A | 12/1991 | Laptewicz, Jr. | |
| 5,733,258 A | 3/1998 | Lane | |
| 5,876,116 A * | 3/1999 | Barker | B01F 33/5011 |
| | | | 366/195 |
| 6,273,898 B1 | 8/2001 | Kienzle et al. | |
| 6,676,664 B1 | 1/2004 | Al-Assir | |
| 6,702,455 B2 | 3/2004 | Vendrely et al. | |
| 6,984,063 B2 * | 1/2006 | Barker | B01F 35/32 |
| | | | 366/139 |
| 7,014,640 B2 | 3/2006 | Kemppainen et al. | |
| 7,112,205 B2 | 9/2006 | Carrison | |
| 7,278,778 B2 | 10/2007 | Sand | |
| 7,311,436 B2 | 12/2007 | Barker et al. | |
| 7,909,833 B2 | 3/2011 | Voellmicke | |
| 8,038,682 B2 | 10/2011 | McGill et al. | |
| 8,308,805 B2 | 11/2012 | Lynn et al. | |
| 8,353,892 B2 | 1/2013 | Thompson et al. | |
| 8,439,930 B2 | 5/2013 | Campion et al. | |
| 8,685,031 B2 | 4/2014 | Kleiner et al. | |
| 8,721,600 B2 | 5/2014 | Henniges et al. | |
| 8,932,295 B1 | 1/2015 | Greenhalgh | |
| 8,945,137 B1 | 2/2015 | Greenhalgh et al. | |
| 8,960,991 B2 | 2/2015 | Vogt et al. | |
| 9,173,694 B2 | 11/2015 | Kleiner | |
| 9,216,096 B2 | 12/2015 | Lynn et al. | |
| 9,456,830 B2 | 10/2016 | Greenhalgh | |
| 9,545,282 B2 | 1/2017 | Mathur et al. | |
| 9,629,968 B2 | 4/2017 | Monterenzi | |
| 9,649,203 B2 | 5/2017 | Lynn et al. | |
| 9,655,748 B2 | 5/2017 | Greenhalgh et al. | |
| 9,668,881 B1 | 6/2017 | Greenhalgh et al. | |
| 9,681,889 B1 | 6/2017 | Greenhalgh et al. | |
| 9,956,019 B2 | 5/2018 | Vogt et al. | |
| 10,004,485 B2 | 6/2018 | Maxwell et al. | |
| 10,123,849 B2 | 11/2018 | Greenhalgh et al. | |
| 10,195,053 B2 | 2/2019 | Kleiner et al. | |
| 10,238,507 B2 | 3/2019 | Greenhalgh et al. | |
| 10,292,747 B2 | 5/2019 | Greenhalgh et al. | |
| 10,321,903 B2 | 6/2019 | Maxwell et al. | |
| 10,405,905 B2 | 9/2019 | Greenhalgh et al. | |
| 10,646,223 B2 | 5/2020 | Zhang et al. | |
| 10,687,879 B2 | 6/2020 | Dewey et al. | |
| 10,729,450 B2 | 8/2020 | Chang et al. | |
| 10,857,001 B2 | 12/2020 | Popejoy et al. | |
| 10,945,860 B2 | 3/2021 | Hay | |
| 11,026,808 B2 | 6/2021 | Glazer et al. | |
| 2004/0122438 A1 | 6/2004 | Abrams | |
| 2004/0193170 A1 | 9/2004 | Kemppainen et al. | |
| 2006/0287641 A1 | 12/2006 | Perlin | |
| 2006/0287642 A1 | 12/2006 | Perlin | |
| 2006/0287643 A1 | 12/2006 | Perlin | |
| 2008/0125856 A1 | 5/2008 | Perez-Cruet et al. | |
| 2010/0249720 A1 | 9/2010 | Biyani et al. | |
| 2011/0082424 A1 | 4/2011 | Barnhouse et al. | |
| 2013/0131683 A1 | 5/2013 | Shah et al. | |
| 2014/0324013 A1 | 10/2014 | Shadeck et al. | |
| 2015/0151041 A1 | 6/2015 | Yodfat et al. | |
| 2017/0304077 A1 | 10/2017 | Shadeck et al. | |
| 2018/0125558 A1 | 5/2018 | Flores et al. | |
| 2018/0303531 A1 | 10/2018 | Sanders et al. | |
| 2019/0029782 A1 | 1/2019 | Jagodinski et al. | |
| 2019/0060086 A1 | 2/2019 | Krause et al. | |
| 2019/0217262 A1 | 7/2019 | McKay | |
| 2020/0229946 A1 | 7/2020 | Greenhalgh et al. | |
| 2020/0237527 A1 * | 7/2020 | Glazer | A61F 2/4425 |
| 2020/0275964 A1 | 9/2020 | Dewey et al. | |
| 2020/0275965 A1 | 9/2020 | Deridder et al. | |
| 2020/0390566 A1 | 12/2020 | Murray et al. | |
| 2021/0052397 A1 | 2/2021 | Popejoy et al. | |
| 2021/0068850 A1 | 3/2021 | Thommen et al. | |
| 2021/0077275 A1 | 3/2021 | Milella, Jr. et al. | |
| 2021/0093367 A1 | 4/2021 | Chukinas | |
| 2021/0179300 A1 * | 6/2021 | Chou | A61M 5/00 |
| 2021/0196477 A1 | 7/2021 | Glazer et al. | |
| 2021/0275323 A1 | 9/2021 | Ono et al. | |

FOREIGN PATENT DOCUMENTS

| | | |
|---|---|---|
| EP | 2 774 583 | 11/2015 |
| EP | 2 330 994 | 5/2016 |
| EP | 2 988 703 | 6/2017 |
| EP | 3 075 359 | 11/2017 |
| EP | 3 305 252 | 5/2019 |
| EP | 3 456 273 | 4/2020 |
| FR | 2 616 169 | 8/1992 |
| FR | 2 846 260 | 4/2004 |
| FR | 2 690 332 | 4/2012 |
| WO | WO 2004/100771 | 11/2004 |
| WO | WO 2005/032336 | 4/2005 |
| WO | WO 2005/048867 | 6/2005 |
| WO | WO 2006/138175 | 12/2006 |
| WO | WO 2008/080590 | 7/2008 |
| WO | WO 2009/116146 | 9/2009 |
| WO | WO 2009/131773 | 10/2009 |
| WO | WO 2009/156718 | 12/2009 |
| WO | WO 2011/109803 | 9/2011 |
| WO | WO 2012/044253 | 4/2012 |
| WO | WO 2014/022750 | 2/2014 |
| WO | WO 2014/072688 | 5/2014 |
| WO | WO 2014/072689 | 5/2014 |
| WO | WO 2014/176526 | 10/2014 |
| WO | WO 2016/127434 | 8/2016 |
| WO | WO 2020/009880 | 1/2020 |
| WO | WO 2020/009882 | 1/2020 |
| WO | WO 2020/034130 | 2/2020 |
| WO | WO 2020/249443 | 12/2020 |
| WO | WO 2020/256125 | 12/2020 |

OTHER PUBLICATIONS

International Search Report and Written Opinion in International Application No. PCT/US2021/020616, dated Jun. 14, 2021.

* cited by examiner

SYSTEMS AND METHODS FOR FILLING MATERIAL

CROSS-REFERENCE TO RELATED APPLICATIONS

This application claims priority benefit to U.S. Provisional Patent Application No. 63/090,072, filed Oct. 9, 2020, the entirety of which is hereby incorporated by reference herein.

BACKGROUND

Field

Some embodiments described herein relate generally to filling assemblies and methods. Specifically, some embodiments of the disclosure relate to devices and methods for loading material into small diameter tubes, including those small diameter tubes used for spinal fusion for delivering graft material, biologics, and/or other material to the disc space.

Description of the Related Art

Advancing age, as well as injury, can lead to degenerative changes in the bones, discs, joints, and ligaments of the spine, producing pain and instability. Under certain circumstances, alleviation of the problems can be provided by performing spinal fusion. Spinal fusion is a surgical technique in which two or more vertebrae of the spinal column are fused together to eliminate the motion between the fused vertebrae. Spinal fusion is used to treat conditions where the spine exhibits instability. Spine instability may result from causes such as fracture, scoliosis, and spondylolisthesis, where one or more vertebrae move in a forward direction relative to the other vertebrae. Spinal fusion with discectomy is also performed for herniation of the discs. This surgery involves removal of the affected disc and fusion of the adjacent vertebrae. Traditionally, bone grafts have been used to fuse the vertebrae, but various types of vertebral implants have also been used.

The use of intervertebral implants and bone screw fixation systems for treating injuries to bones is well established. In most instances, an intervertebral implant is positioned between adjacent vertebrae in the disc space and secured to the bone. The intervertebral implant can be secured to the bone by bone screws or other similar fasteners inserted through holes in the intervertebral implant and into the bone itself. The screws are tightened so that the intervertebral implant holds the bone to be treated in place in order to insure proper healing.

In some spinal fusions, graft material can be inserted within the disc space to restore the height between adjacent vertebrae. In some procedures, other material such as biologics, medicines, and bone morphogenetic protein are inserted within the disc space. Notwithstanding the foregoing, there remains a need for improved methods and devices for filling tubes with material to be delivered to a surgical site.

SUMMARY

In some embodiments, a filling assembly is provided. The filling assembly can include a barrel and receiving block assembly configured to couple to a tube. The filling assembly can include a filling auger. In some embodiments, the filling auger is configured to rotate and translate to fill the tube with material.

In some embodiments, the material comprises biologics, medicine, bone morphogenetic protein, a bone graft, autograft, allograft, xenograft, alloplastic graft, or a synthetic graft. In some embodiments, the filling assembly can include the tube having a diameter to length ratio greater than 1:50 and a maximum diameter of 8 mm. In some embodiments, the tube is configured to deliver material to a surgical site. In some embodiments, the barrel and receiving block assembly comprises a barrel comprising a conical bore and a smaller diameter bore. In some embodiments, the barrel and receiving block assembly comprises a receiving block comprising a larger diameter bore. In some embodiments, the barrel and the receiving block are configured to removably couple to form the barrel and receiving block assembly. In some embodiments, the filling auger comprises a larger diameter flight and a smaller diameter flight. In some embodiments, the barrel and receiving block assembly comprises a larger diameter bore, a conical bore, and a smaller diameter bore. In some embodiments, the filling auger comprises a larger diameter flight configured to be disposed in a larger diameter bore of the barrel and receiving block assembly and a smaller diameter flight configured to be disposed in a smaller diameter bore of the barrel and receiving block assembly. In some embodiments, the filling auger is configured to allow translation within the barrel and receiving block assembly while protruding into a smaller diameter bore of the barrel and receiving block assembly at all times during translation. In some embodiments, the filling assembly can include a gearbox coupled to the filling auger. In some embodiments, the gearbox converts input rotation into combined rotation and translation of the filling auger. In some embodiments, the gearbox comprise a crank configured to translate the filling auger and gears configured to rotate the filling auger.

In some embodiments, a method of filling a tube is provided. The method can include rotating and translating flights of a filling auger within a barrel and receiving block assembly, wherein rotating and translating flights of the filling auger fills a tube with material. The method can include removing the tube from the barrel and receiving block assembly.

In some embodiments, the material comprises biologics, medicine, bone morphogenetic protein, a bone graft, autograft, allograft, xenograft, alloplastic graft, or a synthetic graft. In some embodiments, the method can include loading the tube into a delivery device. In some embodiments, the method can include delivering material to a surgical site with the delivery device. In some embodiments, flights of the filling auger act as a screw conveyer moving material into the tube. In some embodiments, flights of the filling auger act as a pneumatic pump moving material into the tube. In some embodiments, the method can include continuous feeding of material into the barrel and receiving block assembly while the tube is being filled. In some embodiments, the tube is filled without compressing and/or heating the material. In some embodiments, rotating and translating the filling auger comprises rotating and translating the filling auger with a motor. In some embodiments, the filling auger comprises a larger diameter flight rotating and translating within a larger diameter bore of the barrel and receiving block assembly and a smaller diameter flight rotating and translating within a smaller diameter bore of the barrel and receiving block assembly.

DETAILED DESCRIPTION

Figure 1:
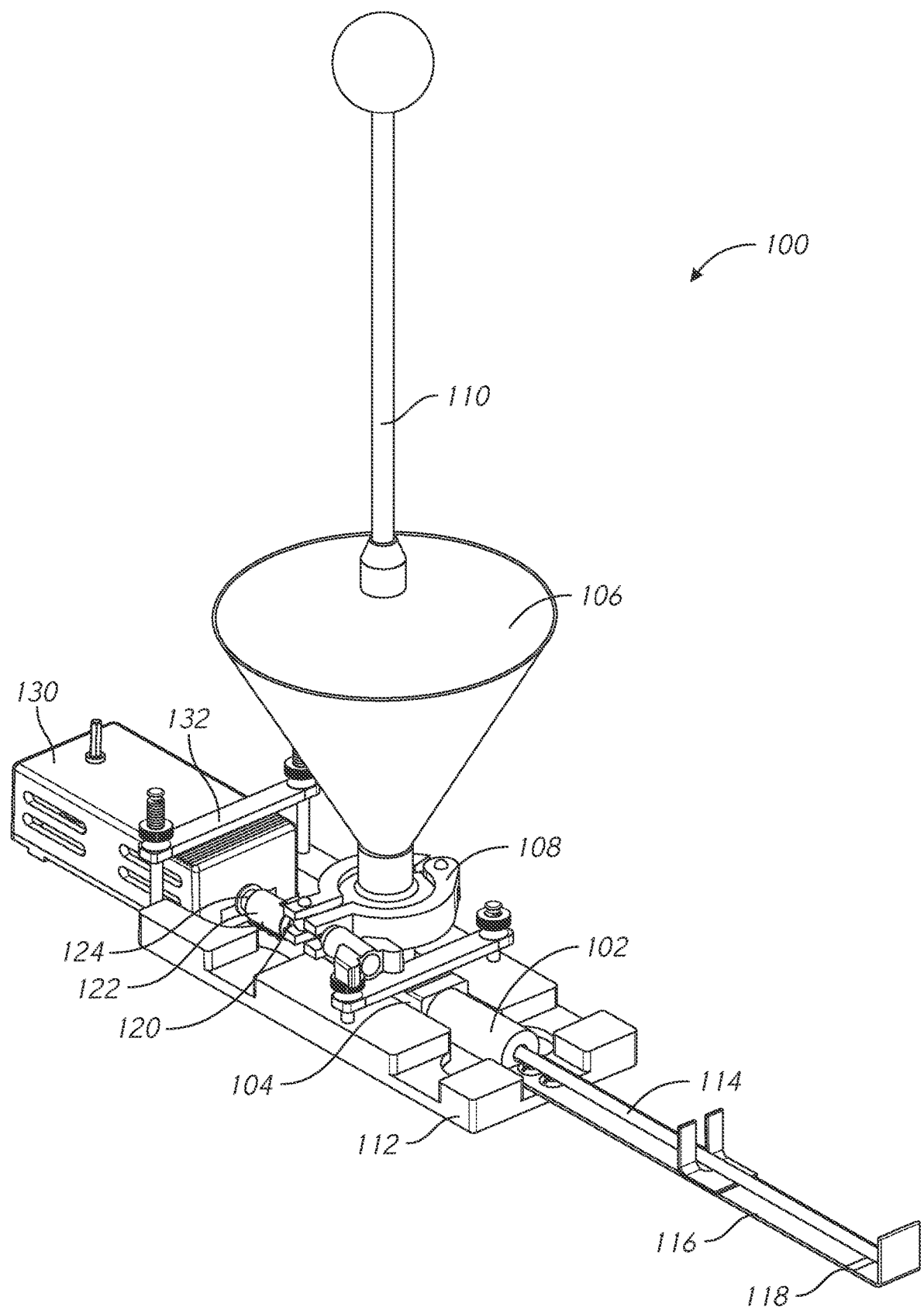
FIG. 1 is a perspective view of an embodiment of a filling assembly.

Although certain preferred embodiments and examples are disclosed below, it will be understood by those in the art that the invention extends beyond the specifically disclosed embodiments and/or uses of the invention and obvious modifications and equivalents thereof. Thus, it is intended that the scope of the invention herein disclosed should not be limited by the particular disclosed embodiments described below.

Filling assemblies can be utilized to load any substance or material to any vessel. As used in this specification, a substance or material can include any biologic and/or chemical substance or material, including, but not limited to, biologics, medicine, bone morphogenetic protein, and/or a bone graft, including, but not limited to, autograft, allograft, xenograft, alloplastic graft, a synthetic graft, and/or combinations of one or more biologics, medicine, bone morphogenetic protein, and/or a bone graft. As used herein, substance and material can be used interchangeably throughout. While specific reference may be made to a substance or material for surgical purposes, the filling assemblies described herein can have non-surgical uses, such as any use to load any substance or material. As used in this specification, a tube can be any structure configured to hold or contain a substance or material, including, but not limited to, cartridge, graft cartridge, needle, vessel, container, and/or conduit. While the tube is shown as having a constant diameter, the tube can have any diameter along the length of the tube. As used herein, tube and cartridge can be used interchangeably throughout. While the tube is shown as being slender or having a small diameter, any size or dimensioned tube can be utilized. While exemplary references are made to the delivery of a substance or material with respect to a surgical site, in some embodiments any site, surgical or non-surgical, can be accessed for the delivery of substances. While specific reference may be made to a vertebra and/or subset and/or grouping of vertebrae, it is understood that any surgical site within the body of the patient can be used.

As disclosed herein, in some embodiments, the filling assemblies can facilitate the filling of small diameter or slender tubes with viscous substance or material. The filling assemblies can include a filling auger with a forward and backward stroke. While not being bound to a theory of the fluid mechanics of the filling assembly, on the forward stroke, the material can generally move forward along the open spaces of the filling auger. The filling auger can act as a screw conveyor for the material as the filling auger rotates. On the forward stroke, the filling auger acts as a pneumatic pump pushing the material forward. On the backward stroke, the material can generally adhere to the walls of the barrel as the filling auger is reversed. In some embodiments, the material is always driven forward. In some embodiments, the material is primarily driven forward. The backward translation of the filling auger cannot pull material back out since the flights are still rotating and serving as a forward screw conveyer. On the subsequent forward stroke, additional material can move into the open spaces of the filling auger thereby pushing more material forward into the tube. By the forward and backward strokes of the filling assembly, material is moved into the tube in a consistent way until the tube is adequately filled.

The filling assemblies, in some embodiments, can generally include a fixture and a mechanism for filling tubes that is powered by hand or by motorized equipment. The filling assemblies can combine the concepts of a mechanical screw conveyor with a pneumatic pump to fill slender tubes with viscous substance or material. The filling assemblies can allow for continuous feeding of the filling material without compressing and/or without heating the material.

The filling assemblies, in some embodiments, can include a shaped bore. The shaped bore generally includes a larger diameter bore, a smaller diameter bore, and a conical bore that extends between the larger diameter and the smaller diameter bores. The smaller diameter bore can have a diameter similar to the tube being filled. Material can be fed into the filling assemblies, such as through an opening that connects to the shaped bore. The filling assemblies, in some embodiments, can include a filling auger at least partially disposed within the shaped bore. The filling auger can include fighting that acts as a screw conveyer to move material toward the tube. The filling auger can include a larger diameter flight and a smaller diameter flight. The larger diameter flight of the filling auger rotates and translates within the larger diameter bore. The smaller diameter flight of the filling auger rotates and translates within the smaller diameter bore. The filling auger is sized to allow for rotation and translation within the shaped bore, while always having the smaller diameter flight of the filling auger within the smaller diameter bore.

The filling auger is coupled to a gearbox. The gearbox converts rotational movement into combined rotational and translational movement of the filling auger. The gearbox can include a crank that drives the filling auger forwards and backwards. The gearbox can cause simultaneous rotation and translation of the filling auger. The rotation of the flights of the filling auger can act as a screw conveyer. The rotation moves material through the shaped bore and into the tube. The length of the filling auger within the smaller diameter bore creates a pneumatic seal with the material. The forward translation of the filling auger pneumatically drives the material forward within the shaped bore and the tube being filled. In some embodiments, the material is always driven forward. In some embodiments, the material is primarily driven forward. The backward translation of the filling auger does not pull the material back since the flights are still rotating and serving as a forward screw conveyor. In some embodiments, the translation and rotation rates are equal to or lower than the pitch of the filling auger.

Although referred to as filling assemblies, these devices need not be used for the filling of materials. The filling auger, including the forward and backward strokes directed by the gearbox can be used for any purpose not limited to filling tubes. The filling auger can be used to move any material, including viscous material, via the screw conveyer. The filling auger can be used to move any material, including viscous material, via the pneumatic pump.

Figure 2:
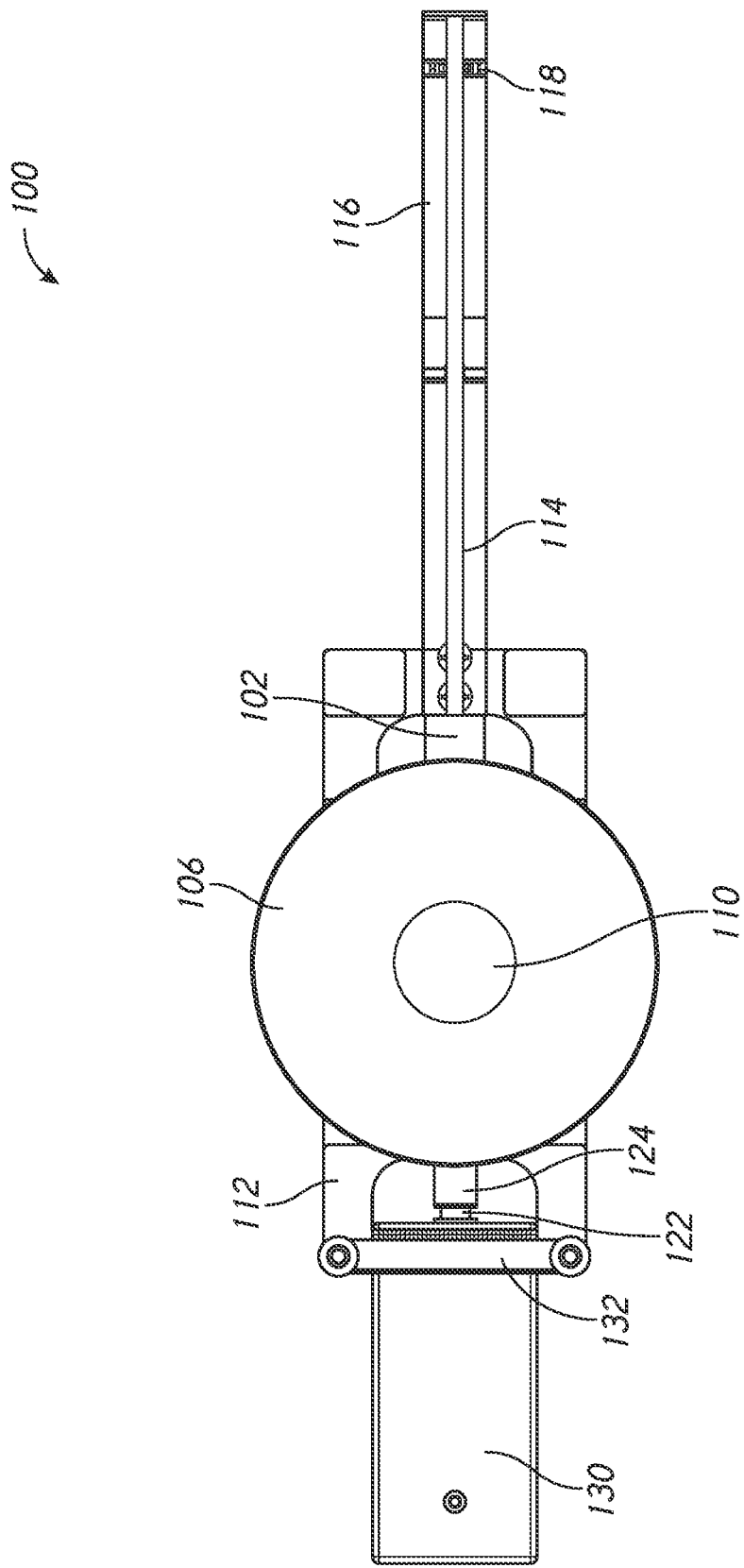
FIG. 2 is a top view of the filling assembly of FIG. 1.
Figure 3:
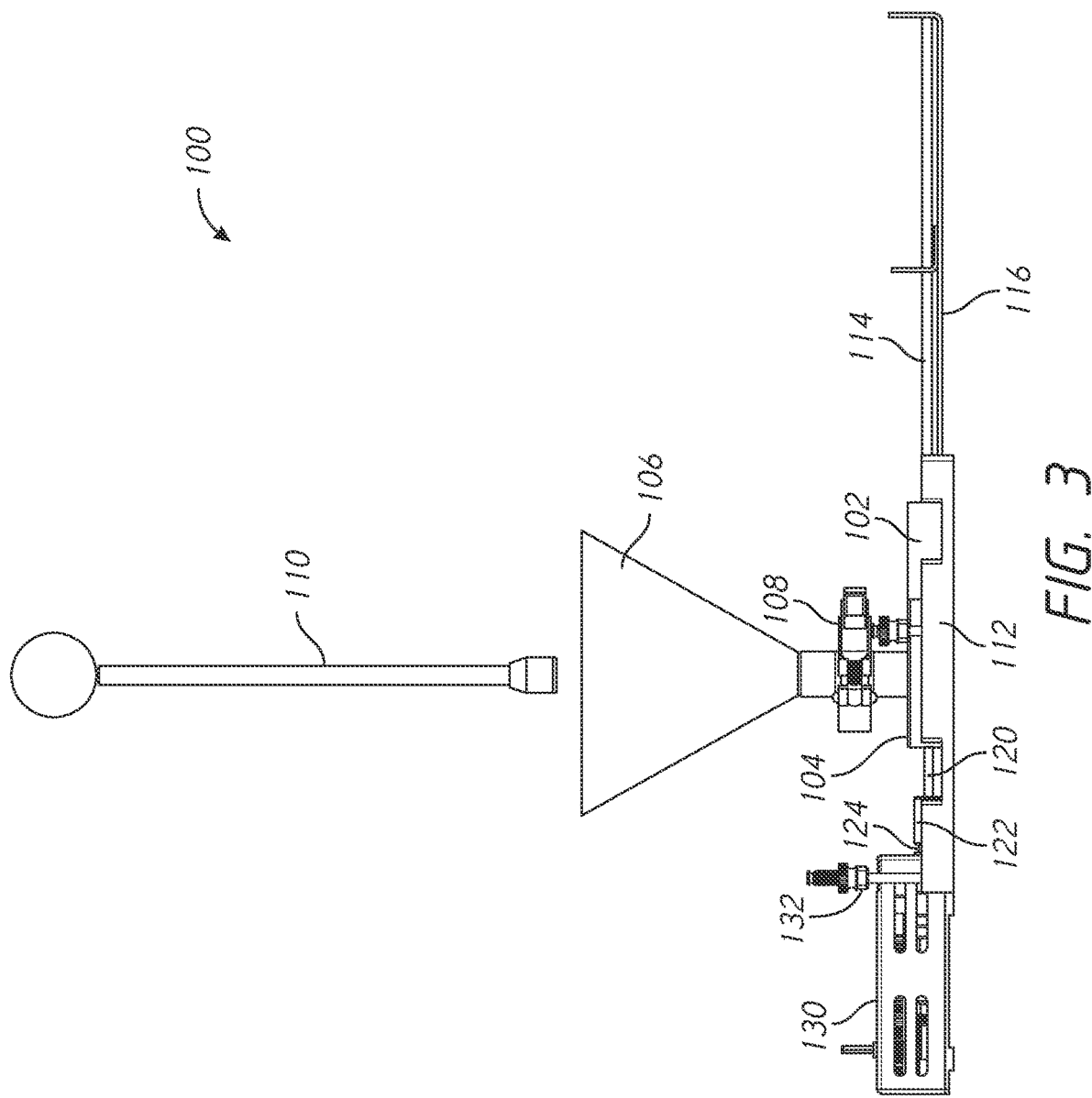
FIG. 3 is a side view of the filling assembly of FIG. 1.
Figure 4:
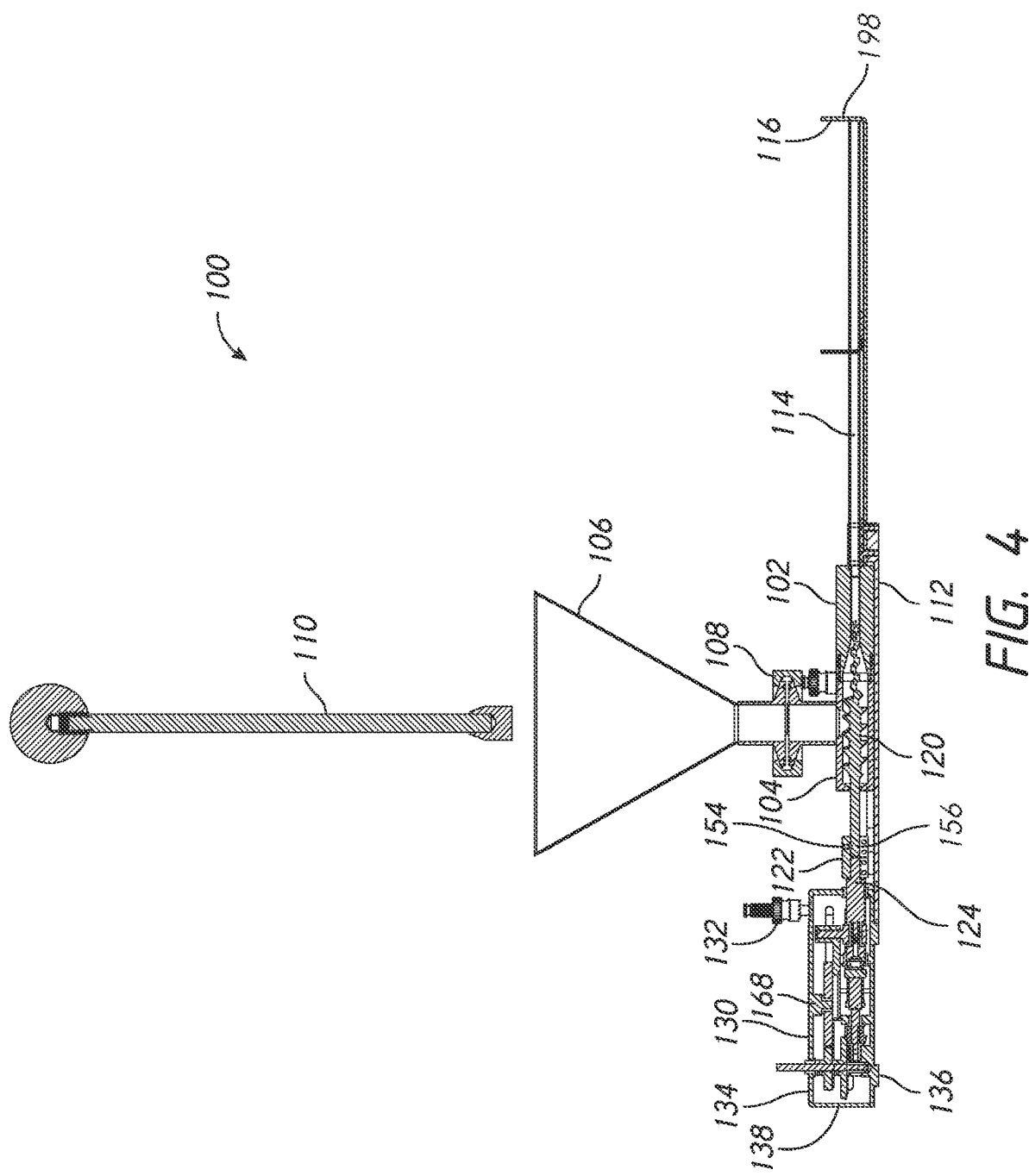
FIG. 4 is a cross-sectional side view of the filling assembly of FIG. 1.
Figure 5:
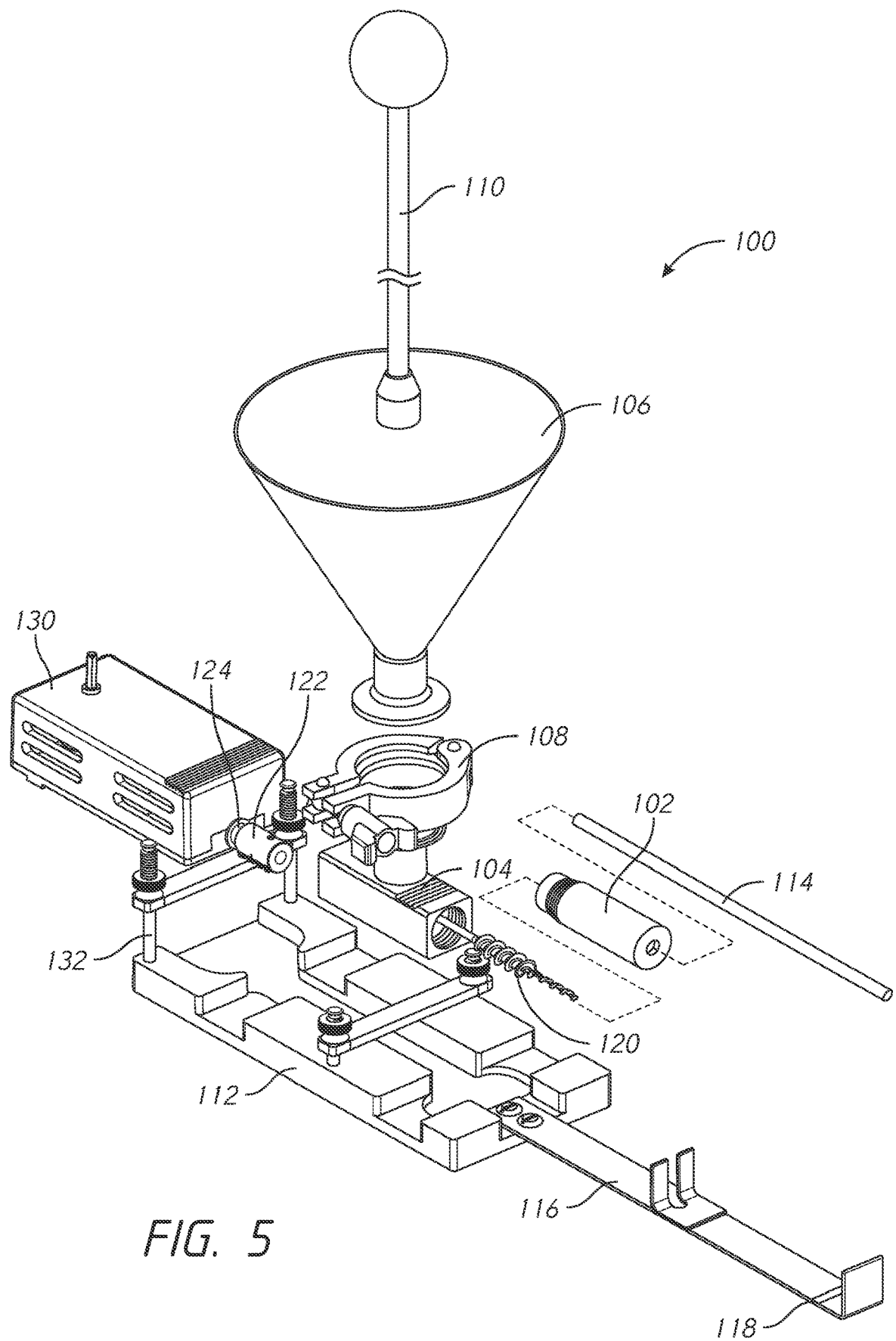
FIG. 5 is an exploded perspective view of the filling assembly of FIG. 1.

FIG. 1 shows a perspective view of an embodiment of a filling assembly 100. FIG. 2 shows a top view of the filling assembly 100. FIG. 3 shows a side view of the filling assembly 100. FIG. 4 shows a cross-sectional view of the filling assembly 100. FIG. 5 is an exploded perspective view of the filling assembly 100.

As shown in FIGS. 1-5, the filling assembly 100 can include a barrel 102. The barrel 102 can have a cavity that forms an elongate pathway. The shape of the elongate pathway of the barrel 102 can facilitate the movement of material, as described herein. The filling assembly 100 can include a receiving block 104. The receiving block 104 can have a cavity that forms an elongate pathway. The shape of the elongate pathway of the receiving block 104 can facilitate the movement of material, as described herein. In some embodiments, the barrel 102 and the receiving block 104 can be coupled. In some embodiments, the barrel 102 and the receiving block 104 can be integrally or monolithically formed. In some embodiments, the barrel 102 and the receiving block 104 can form a unitary assembly. In some embodiments, the barrel 102 and the receiving block 104 can form a continuous bore.

In some embodiments, the barrel 102 and the receiving block 104 are removably coupled. In some embodiments, the barrel 102 can include male threads and the receiving block 104 can include female threads. In some embodiments, the elongate pathway of the barrel 102 can correspond to the tube to be filled. In some embodiments, two or more different barrels 102 can couple to the receiving block 104. The two or more different barrels 102 can correspond to two or more different diameter tubes. The user can select the barrel 102 corresponding to the tube to be filled.

The receiving block 104 can allow a user to feed material into the filling assembly 100. The filling assembly 100 can include a funnel top 106. The filling assembly 100 can include a clamp 108 to position the funnel top 106. The filling assembly 100 can include a plunger 110. The receiving block 104 can have an opening to allow material to pass into the receiving block 104 from the funnel top 106. The clamp 108 can securely couple the funnel top 106 to the filling base 112. The filling base 112 can be any fixture to hold in position the various components including the barrel 102, the receiving block 104, and the funnel top 106. In some embodiments, the user can manipulate the plunger 110 to push material from the funnel top 106 toward the receiving block 104. In some embodiments, the plunger is automatically manipulated such as by an end effector of a robot.

The filling assembly 100 can be utilized in combination with a tube 114. In some embodiments, the filling assembly 100 is reusable. In some embodiments, the tube 114 is reusable. In some methods of use, the tube 114 is disposable. The filling assembly 100 can be utilized to fill two or more tubes 114. The filling assembly 100 can consecutively fill tubes 114. The filling assembly 100 can allow the tube 114 to be easily loaded. The filling assembly 100 can allow the tube 114 to be easily removed once filled.

The tube 114 can be slender. The tube 114 can have an inner diameter of 3 mm, 4 mm, 5 mm, 6 mm, 7 mm, 8 mm, between 3 mm and 8 mm, between 4 mm and 6 mm, or any value or range of values between 3 mm and 10 mm, less than 3 mm, less than 4 mm, less than 5 mm, less than 6 mm, less than 7 mm, less than 8 mm, greater than 3 mm, greater than 4 mm, greater than 5 mm, greater than 6 mm, greater than 7 mm, or greater than 8 mm. The tube 114 can have a maximum diameter of 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, or any range of two of the foregoing values. In some embodiments, the inner diameter of the tube 114 is 5 mm. The tube 114 can be configured to deliver material to a surgical site.

The tube 114 can have a length of 50 mm, 75 mm, 100 mm, 125 mm, 150 mm, 175 mm, 200 mm, 225 mm, 250 mm, 275 mm, 300 mm, 325 mm, 350 mm, 375 mm, 400 mm, 425 mm, 450 mm, 475 mm, 500 mm, between 200 mm and 300 mm, between 250 mm and 350 mm, or any value or range of values between 50 mm and 500 mm, less than 300 mm, less than 350 mm, less than 400 mm, less than 450 mm, less than 500 mm, greater than 100 mm, greater than 150 mm, greater than 200 mm, greater than 250 mm, greater than 300 mm, or greater than 350 mm. In some embodiments, the length of the tube 114 is 279.4 mm (11 inches).

The tube 114 can have a diameter to length ratio. The diameter to length ratio of the tube 114 can be 1:10, 1:20, 1:30, 1:40, 1:50, 1:60, 1:70, 1:80, 1:90, 1:100, 1:110, 1:120, 1:130, 1:140, 1:150, 1:160, 1:170, 1:180, 1:190, 1:200, or any value or range of values between 1:10 and 1:200, greater than 1:20, greater than 1:30, greater than 1:40, greater than 1:50, greater than 1:60, greater than 1:70, greater than 1:80, greater than 1:90, greater than 1:100, less than 1:100, less than 1:120, less than 1:140, less than 1:160, less than 1:180, or less than 1:200. The tube 114 can have a length that is approximately or at least 10 times the diameter of the tube, approximately or at least 20 times the diameter of the tube, approximately or at least 30 times the diameter of the tube, approximately or at least 40 times the diameter of the tube, approximately or at least 50 times the diameter of the tube, approximately or at least 60 times the diameter of the tube, approximately or at least 70 times the diameter of the tube, approximately or at least 80 times the diameter of the tube, approximately or at least 90 times the diameter of the tube, approximately or at least 100 times the diameter of the tube, or any value or range of values between a length that is approximately or at least 10 times the diameter of the tube and approximately or at least 100 times the diameter of the tube. In some embodiments, the diameter to length ratio of the tube 114 is approximately 1:50, with the length being about 50 times the diameter of the tube 114.

The tube 114 can be configured to hold material. The tube 114 can have volume. The volume can be 2 cc, 3 cc, 4 cc, 5 cc, 6 cc, 7 cc, 8 cc, 9 cc, 10 cc, or any value or range of values between 2 cc and 10 cc, less than 2 cc, less than 3 cc, less than 4 cc, less than 5 cc, less than 6 cc, less than 7 cc, less than 8 cc, less than 9 cc, less than 10 cc, greater than 2 cc, greater than 3 cc, greater than 4 cc, greater than 5 cc, greater than 6 cc, greater than 7 cc, greater than 8 cc, greater than 9 cc, or greater than 10 cc.

The tube 114 can have an inner diameter and length appropriate for use in surgical procedures. The tube 114 can have an inner diameter and length appropriate for delivery of material during a spinal surgery. The tube 114 can have an inner diameter and length to maintain a reasonable volume. The tube 114 can have an inner diameter and length appropriate to minimize tissue disruption.

The tube 114 can be filled with material as described herein. The material can have a high viscosity. The material can have a viscous consistency. The material can be demineralized bone matrix (DBM). The material can be any material typically used for spinal surgery. The material can be moldable by hand. The material can be capable of being packed into spinal devices such as spinal cages. The material can be capable of being packed into and around the anatomy of the patient.

The tube 114 can be removably inserted into the barrel 102. The barrel 102 can have a cavity to accept the tube 114. The filling assembly 100 can include a support bracket 116. The support bracket 116 can align the tube 114 with the cavity of the barrel 102. The support bracket 116 can hold the tube 114 level. The support bracket 116 can support the tube 114 as the tube 114 is filled with material. The support bracket 116 can include a slotted support. The support bracket 116 can include a groove. The support bracket 116 can allow the tube 114 to be loaded from the top of the support bracket 116. The support bracket 116 can allow the tube 114 to be easily loaded. The support bracket 116 can allow the tube 114 to be easily unloaded. In some embodiments, the support bracket 116 and the filling base 112 can be coupled. In some embodiments, the support bracket 116 and the filling base 112 are coupled via one or more fasteners. In some embodiments, the support bracket 116 and the filling base 112 can be integrally or monolithically formed.

The support bracket 116 can include one or more indicia 118. The indicia 118 can indicate the distal position of the material within the tube 114. The indicia 118 can indicate when a tube 114 is full. In the illustrated embodiment, the indicia 118 indicates the fill zone. The indicia 118 can include one or more icons. The indicia 118 can include one or more lines. The indicia 118 can include one or more letters or numbers. The indicia 118 can include a scale.

The filling assembly 100 can include a filling auger 120. The filling auger 120 can include flighting. The filling auger 120 can include one or more flights. The filling auger 120 can include two flights. The filling auger 120 can extend into the barrel 102. The filling auger 120 can extend through the receiving block 104. The filling auger 120 can extend proximally from the receiving block 104. The shape of the filling auger 120 can facilitate the movement of material, as described herein. The filling base 112 can include one or more cutouts to allow the user to view the filling auger 120.

The filling assembly 100 can include a shaft coupling 122. The shaft coupling 122 can be any mechanical means that allows for the transmission of rotational force. The shaft coupling 122 can be any mechanical means that allows for the transmission of translational force. The shaft coupling 122 can rigidly join two shafts. The shaft coupling 122 can couple to the filling auger 120.

The filling assembly 100 can include an output shaft 124. The output shaft 124 can transmit rotational and translational force from an input shaft, as described herein. The output shaft 124 can be powered by gears, as described herein. The shaft coupling 122 can couple to the output shaft 124. The output shaft 124 can be coupled to the filling auger 120 via the shaft coupling 122.

The filling assembly 100 can include a gearbox 130. In some embodiments, the gearbox 130 and the filling base 112 can be coupled. In some embodiments, the filling assembly 100 include a gearbox bracket 132. In some embodiments, the gearbox bracket 132 can secure the gearbox 130 to the filling base 112. The gearbox bracket 132 can be any fixture to hold gearbox 130 in position relative to other components of the filling assembly 100. The gearbox 130 can include a housing 134 as shown in FIG. 4. The housing 134 can cover gears and other components of the gearbox 130. The gearbox can include a gearbox base 136. In some embodiments, the housing 134 and the gearbox base 136 are coupled via one or more fasteners. In some embodiments, the housing 134 and the gearbox base 136 can be integrally or monolithically formed.

The gearbox 130 can rotate the filling auger 120. The gearbox 130 can rotate the filling auger 120 during a forward stroke as described herein. The gearbox 130 can rotate the filling auger 120 during a backward stroke as described herein. The gearbox 130 can rotate the filling auger 120 during a forward stroke in a clockwise direction. The gearbox 130 can rotate the filling auger 120 during a backward stroke in a clockwise direction. The gearbox 130 can rotate the filling auger 120 in the same direction during the forward and backward stroke. The filling auger 120 can have a left hand pitch. The filling auger 120 can be designed to move material forward upon rotation in the clockwise direction. The filling assembly 100 can include a proximal end 138 and a distal end 198. During the forward stroke, the filling auger 120 can move distally. The filling auger 120 can move toward the distal end of the tube 114 to be filled during the forward stroke. During the backward stroke, the filling auger 120 can move proximally. The filling auger 120 can move away from the distal end of the tube 114 to be filled during the backward stroke. In some embodiments, the translation of the filling auger 120 does the majority of the work moving the material. In some embodiments, the rotation of the filling auger 120 does the majority of the work moving the material. In some embodiments, the rotation and the translation of the filling auger 120 moves the material in combination. In some embodiments, the rotation and the translation of the filling auger 120 moves the material equally, in combination.

Figure 6:
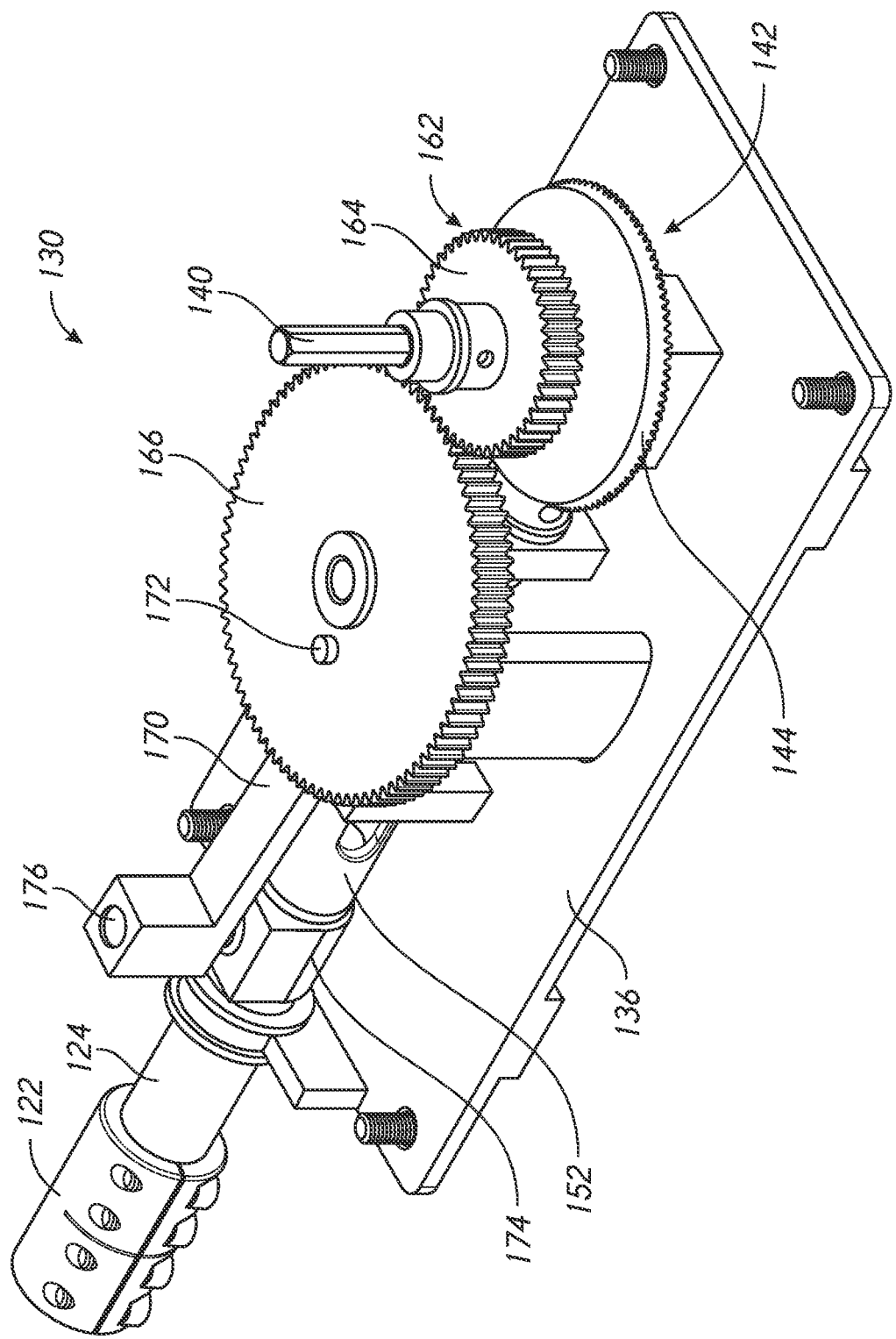
FIG. 6 is a perspective view of the gear box of FIG. 1 with the top housing removed.
Figure 7:
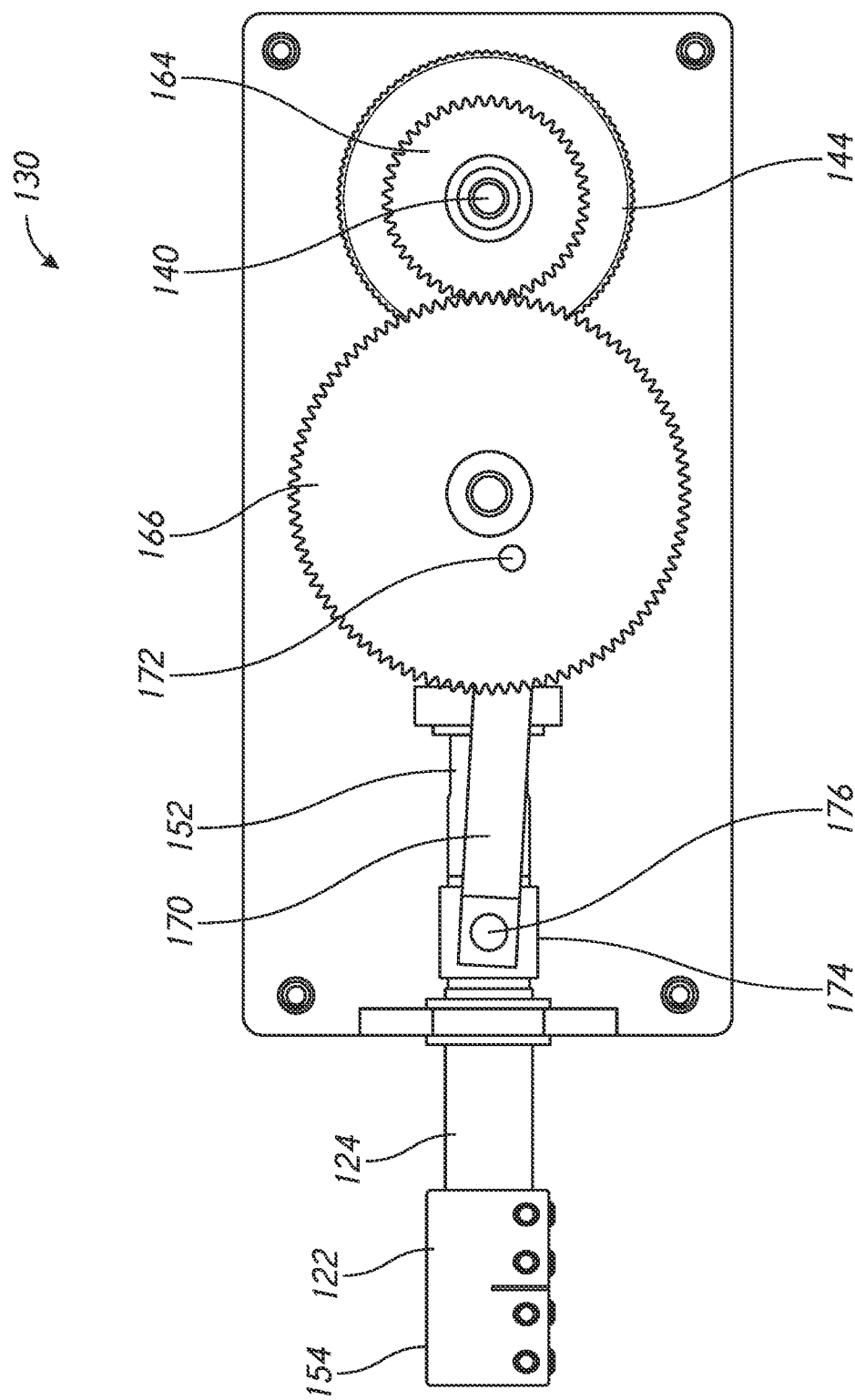
FIG. 7 is a top view of the gear box of FIG. 6 with the top housing removed.
Figure 8:
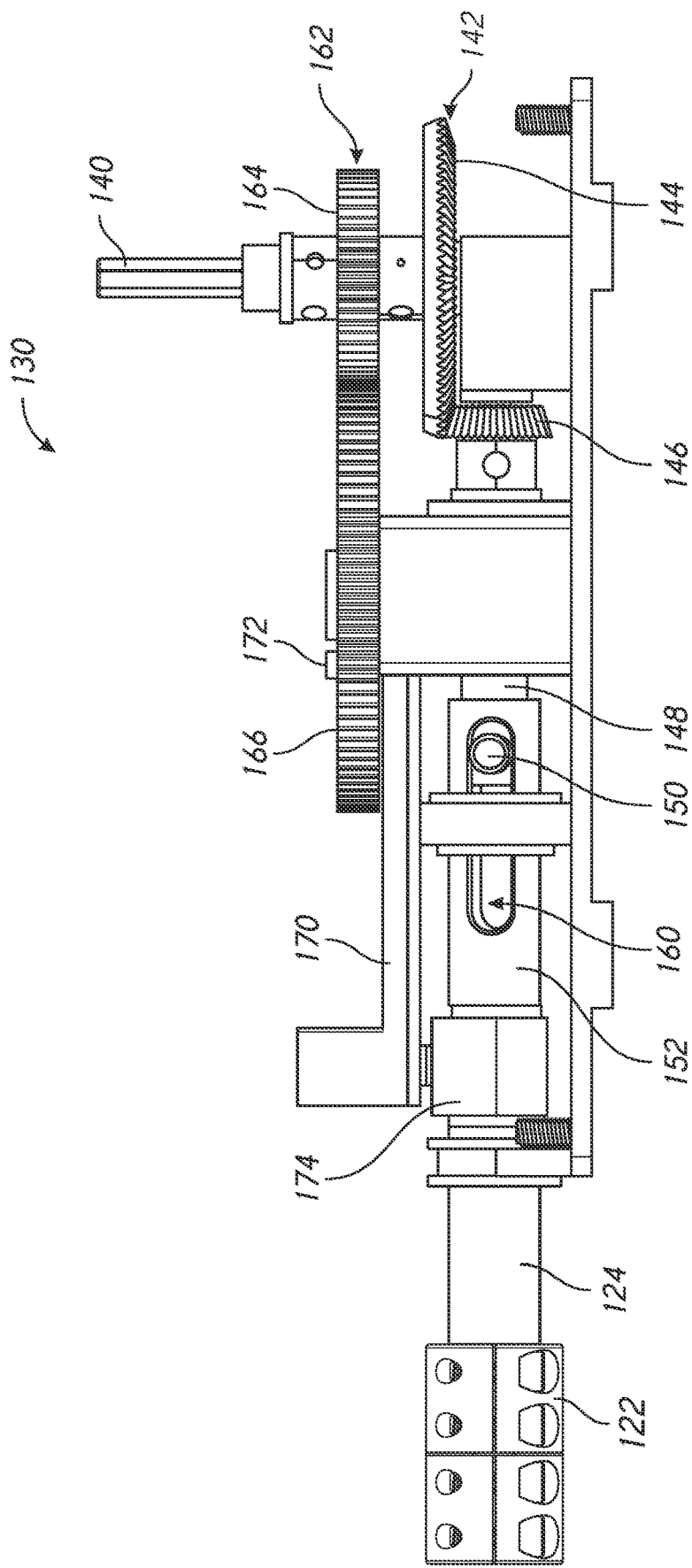
FIG. 8 is a side view of the gear box of FIG. 6 with the top housing removed.
Figure 9:
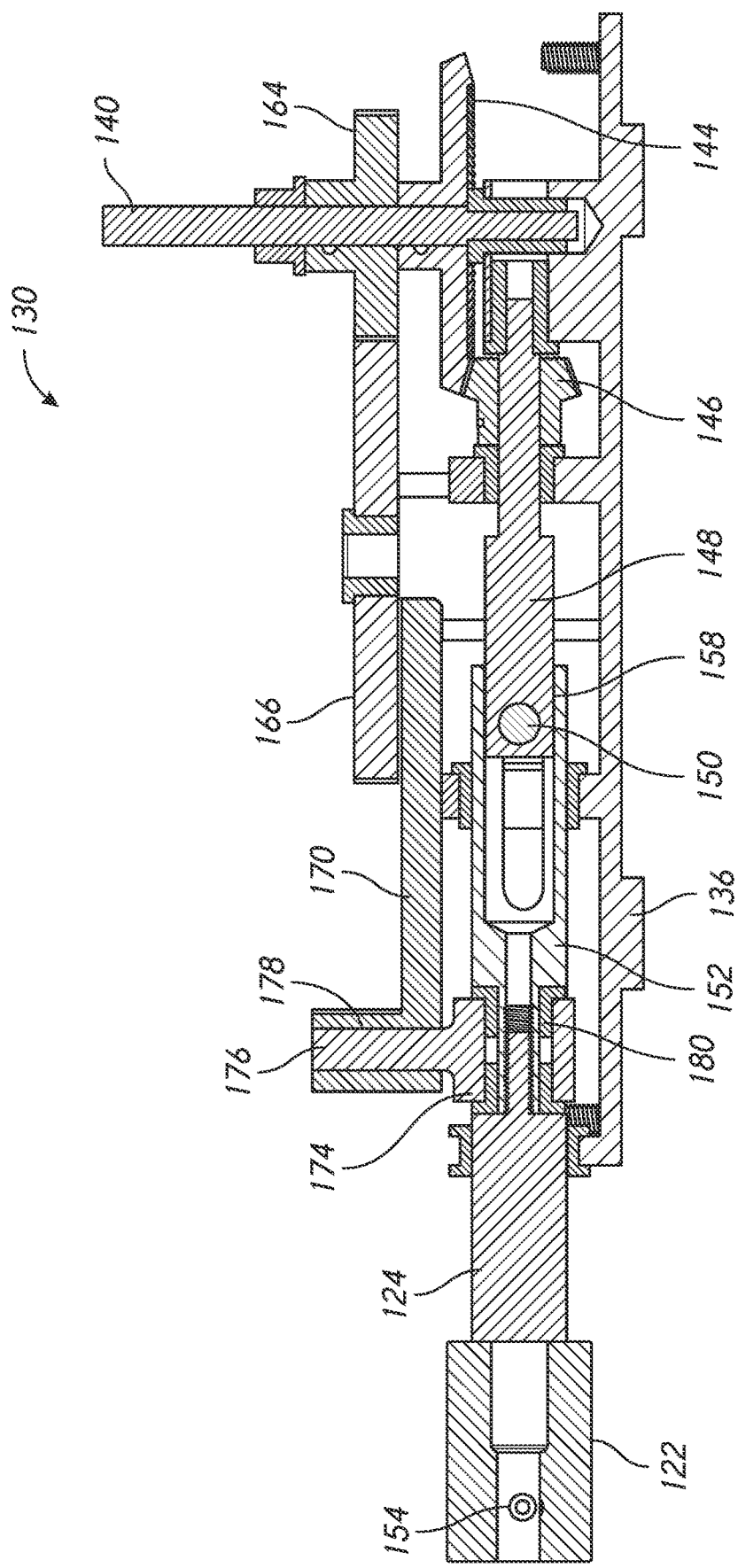
FIG. 9 is a cross-sectional side view of the gear box of FIG. 6 with the top housing removed.
Figure 10:
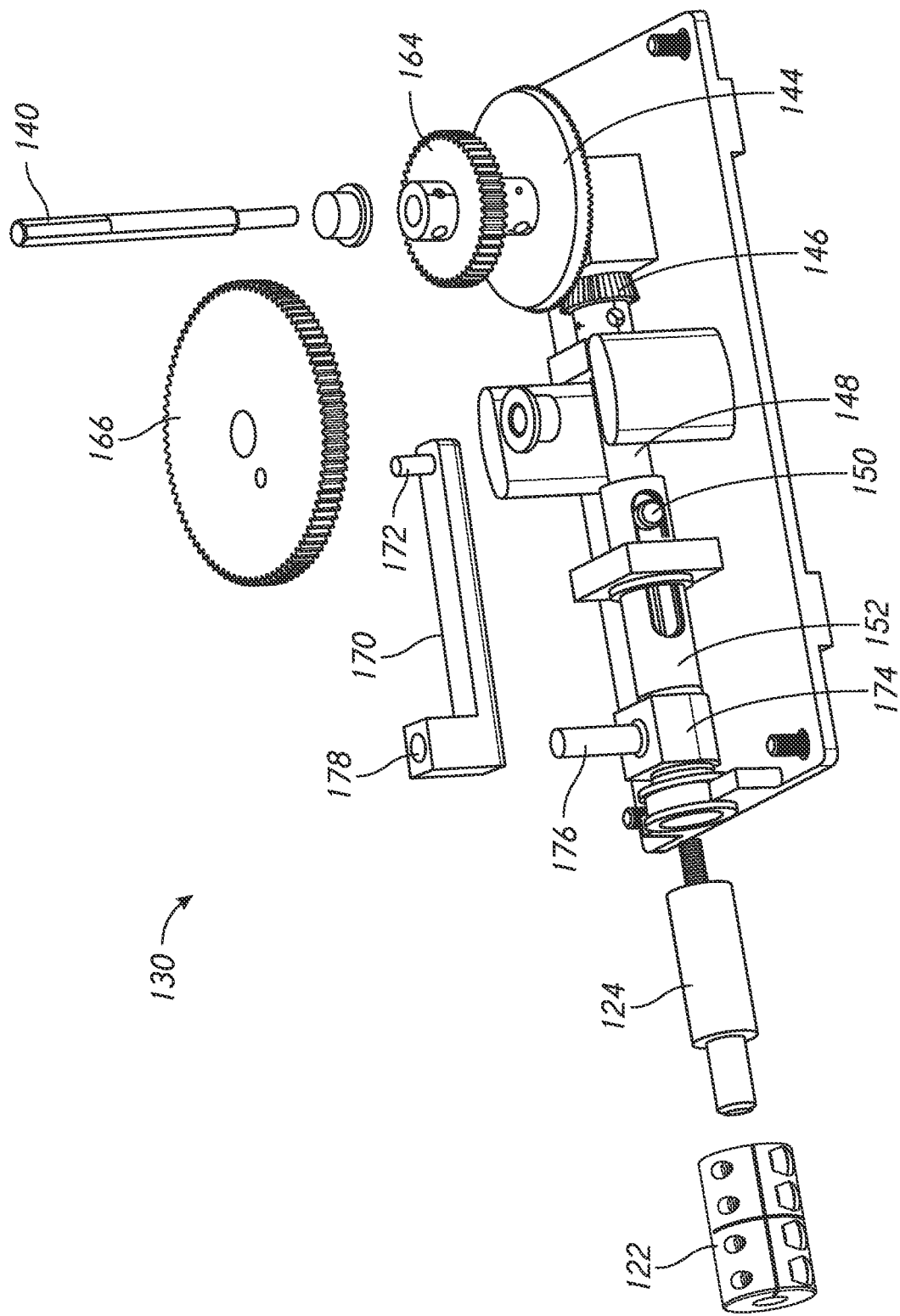
FIG. 10 is an exploded perspective view of the gear box of FIG. 6 with the top housing removed.

FIG. 6 shows a perspective view of the gearbox 130. FIG. 7 shows a top view of the gearbox 130. FIG. 8 shows a side view of the gearbox 130. FIG. 9 shows a cross-sectional view of the gearbox 130. FIG. 10 is an exploded perspective view of the gearbox 130.

FIGS. 6-10 illustrate the gearbox 130. The housing 134 shown in FIG. 4 is removed to show the internal components of the gearbox 130. The gearbox 130 can include an input shaft 140. In some embodiments, the input shaft 140 can be rotated manually. The input shaft 140 can be rotated by the user. In some embodiments, the input shaft 140 can be rotated automatically. The input shaft 140 can be rotated by a motor. The input shaft 140 can be keyed. The input shaft 140 can have a polygonal shape. The input shaft 140 can be any shape to transmit torque to the gears of the gearbox 130.

The gearbox 130 can rotate clockwise. The filling auger 120 can have a left hand pitch on the filling auger 120 to result in forward motion. A clockwise gearbox rotation can be coupled with a left hand pitch auger to result in forward motion. In other embodiments, the gearbox 130 can rotate counter-clockwise. The filling auger 120 can have a right hand pitch (not shown) on the filling auger 120 to result in forward motion. A counter-clockwise gearbox rotation can be coupled with a right hand pitch auger to result in forward motion.

The gearbox 130 can include a rotation mechanism 142. The rotation mechanism 142 can be any mechanism that cause the rotation of the filling auger 120 as a result of the rotation of the input shaft 140. While the rotation mechanism 142 is described below in relation to bevel gears, the rotation mechanism 142 can include any gear system. While the rotation mechanism 142 is described below in relation to several shafts, the rotation mechanism 142 can have any component that enables the transmission of torque.

The gearbox 130 can include a bevel gear 144. The bevel gear 144 can be mounted on the input shaft 140. Rotation of the input shaft 140 can cause similar rotation of the bevel gear 144. The bevel gear 144 can have any diameter. In the illustrated embodiment, the bevel gear 144 is 1.5" in diameter. The bevel gear 144 can have any number of teeth. The gearbox 130 can include any number of bushings to facilitate the coupling of components. The gearbox 130 can include a bushing to facilitate coupling the bevel gear 144 and the input shaft 140. As the input shaft 140 rotates, the bevel gear 144 rotates.

The gearbox 130 can include a secondary bevel gear 146. The bevel gear 144 and the secondary bevel gear 146 can have axes that intersect. The bevel gear 144 and the secondary bevel gear 146 can be mounted on shafts that are perpendicular. The secondary bevel gear 146 can be mounted on a rotating shaft 148. The rotating shaft 148 can be 90 degrees offset from the input shaft 140. The gearbox 130 can include a bushing to facilitate coupling the secondary bevel gear 146 and the rotating shaft 148. As the bevel gear 144 rotates, the secondary bevel gear 146 rotates. As the secondary bevel gear 146 rotates, the rotating shaft 148 rotates.

The secondary bevel gear 146 can have any diameter. In the illustrated embodiment, the secondary bevel gear 146 is 0.5" in diameter. The secondary bevel gear 146 can have any number of teeth. Depending on the teeth of the bevel gear 144 and secondary bevel gear 146, the input shaft 140 and the rotating shaft 148 can rotate at different speeds. In the illustrated embodiment, the rotating shaft 148 rotates faster than the input shaft 140. In the illustrated embodiment, the rotating shaft 148 rotates three times faster than the input shaft 140. The tooth bearing surfaces of bevel gear 144 and the secondary bevel gear 146 can be conical. The bevel gear 144 can have a 1.5" pitch diameter. The secondary bevel gear 146 can have a 0.4" pitch diameter. The ratio or rotation of the bevel gear 144 to the secondary bevel gear 146 can be 1:3. One rotation of the bevel gear 144 can cause three rotations of the secondary bevel gear 146.

The rotating shaft 148 can include a transfer pin 150. In some embodiments, the transfer pin 150 can be disposed within a bore of the rotating shaft 148. The transfer pin 150 can extend through the rotating shaft 148. In some embodiments, the transfer pin 150 is integrally or monolithically formed with the rotating shaft 148. As the rotating shaft 148 rotates, the transfer pin 150 rotates.

The gearbox 130 can include a translating shaft 152. The translating shaft 152 can include a lumen 158. The lumen 158 can be sized to receive a portion of the rotating shaft 148 therein. The translating shaft 152 can include a slot 160. The slot 160 can be sized to receive the transfer pin 150. The transfer pin 150 can transmit torque between the rotating shaft 148 and the translating shaft 152. As the rotating shaft 148 rotates, the translating shaft 152 rotates.

The gearbox 130 can include the output shaft 124. The output shaft 124 can extend from the gearbox 130 as illustrated in FIGS. 1-5. In some embodiments, the output shaft 124 and the translating shaft 152 can be coupled. In some embodiments, the output shaft 124 can include male threads and the translating shaft 152 can include female threads. In some embodiments, the output shaft 124 and the translating shaft 152 can be integrally or monolithically formed.

The gearbox 130 can include the shaft coupling 122. The shaft coupling 122 can couple the output shaft 124 and the filling auger 120. The shaft coupling 122 can include a clamp. The shaft coupling 122 can be tightened onto the output shaft 124. The shaft coupling 122 can be tightened onto filling auger 120. As the output shaft 124 rotates, the shaft coupling 122 rotates. As the shaft coupling 122 rotates, the filling auger 120 rotates. As the output shaft 124 rotates, the filling auger 120 rotates, due to the coupling of these components by the shaft coupling 122.

The gearbox 130 can include a ball plunger 154. In some embodiments, the ball plunger 154 can be disposed within a bore of the shaft coupling 122. The ball plunger 154 can be threaded and the bore of the shaft coupling 122 can be threaded. The ball plunger 154 can include a ball end. The filling auger 120 can include a circumferential groove 156 as shown in FIG. 4. The ball end of the ball plunger 154 can be disposed within the circumferential groove 156 of the filling auger 120. The ball plunger 154 gives the user tactile feedback to know when the filling auger 120 is fully seated in the shaft coupling 122. The ball plunger 154 engages the circumferential groove 156 when the filling auger 120 is properly positioned within the shaft coupling 122. The ball plunger 154 engages the circumferential groove 156 when the correct length of the shaft of the filling auger 120 is inserted into the shaft coupling 122. The ball plunger 154 reduces the potential for operator error during setup. The ball plunger 154 ensures that the shaft of the filing auger 120 is not clamped in at an inappropriate length resulting in damage to the filling assembly 100. The shaft coupling 122 can facilitate alignment of the shaft of the filing auger 120. The ball plunger 154 can facilitate the proper length of the shaft of the filling auger 120 is inserted into the shaft coupling 122. The ball plunger 154 functions as a length confirmation between components of the filling assembly 100.

The rotation of the filling auger 120 is the result of the rotation of the input shaft 140. The input shaft 140 rotates the bevel gear 144 which rotates the secondary bevel gear 146. The secondary bevel gear 146 can be mounted on a rotating shaft 148 which rotates with the secondary bevel gear 146. The rotating shaft 148 rotates the translating shaft 152 which rotates the output shaft 124. The output shaft 124 rotates the shaft coupling 122 and the filling auger 120. The gear ratio between the bevel gear 144 and the secondary bevel gear 146 determines the rotational speed of the filling auger 120 relative to the input shaft 140.

The gearbox 130 can include a translation mechanism 162. The translation mechanism 162 can be any mechanism that causes the translation of the filling auger 120 as a result of the rotation of the input shaft 140. While the translation mechanism 162 is described below in relation to spur gears, the translation mechanism 162 can include any gear system. While the translation mechanism 162 is described below in relation to several shafts, the rotation mechanism 142 can have any component that enables the transmission of translational movement. While the rotation mechanism 142 and the translation mechanism 162 are driven by a common input shaft 140 as illustrated, the rotation mechanism 142 and the translation mechanism 162 can be driven by separate input shafts. The rotation mechanism 142 and the translation mechanism 162 can be coupled or uncoupled.

The gearbox 130 can include a spur gear 164. The spur gear 164 can be mounted on the input shaft 140. In the illustrated embodiment, the spur gear 164 is mounted above the bevel gear 144. In the illustrated embodiment, the spur gear 164 is smaller in diameter than the bevel gear 144. Rotation of the input shaft 140 can cause similar rotation of the spur gear 164. The spur gear 164 can have any diameter. In the illustrated embodiment, the spur gear 164 is 1" in diameter. The spur gear 164 can have any number of teeth. The gearbox 130 can include any number of bushings to facilitate the coupling of components. The gearbox 130 can include a bushing to facilitate coupling the spur gear 164 and the input shaft 140. As the input shaft 140 rotates, the spur gear 142 rotates.

The gearbox 130 can include a secondary spur gear 166. The spur gear 164 and the secondary spur gear 166 can have axes that are parallel. The spur gear 164 and the secondary spur gear 166 can be mounted on shafts that are parallel. The secondary spur gear 166 can be mounted on a stationary shaft 168. In some embodiments, the stationary shaft 168 can be coupled to the housing 134 as shown in FIG. 4. In some embodiments, the stationary shaft 168 is monolithically or integrally formed with the housing 134. The gearbox 130 can include a bushing to facilitate coupling the secondary spur gear 166 and the stationary shaft 168.

The gearbox 130 can include a driving arm 170. The driving arm can include an axle 172. The secondary spur gear 166 can include a bore. The axle 172 of the driving arm 170 can be disposed within the bore of the secondary spur gear 166. As the secondary spur gear 166 rotates, the driving arm 170 translates distally and proximally. The axle 172 can act as a crank. The axle 172 can be disposed at a right angle to the driving arm 170. The axle 172 can impart a circular motion to the driving arm 170 as the secondary spur gear 166 is rotated.

The gearbox 130 can include a transfer collar 174. The transfer collar 174 can include an axle 176. The driving arm 170 can include a bore 178. The axle 176 of the transfer collar 174 can be disposed within the bore 178 of the driving arm 170. As the driving arm 170 translates, the transfer collar 174 translates distally and proximally. The driving arm 170 can be used to convert rotational motion of the secondary spur gear 166 into translational motion of the transfer collar 174.

The transfer collar 174 can couple to the translating shaft 152. The gearbox 130 can include a bushing to facilitate coupling the transfer collar 174 and the translating shaft 152. The transfer collar 174 can abut the translating shaft 152 such that distal and proximal movement of the transfer collar 174 causes distal and proximal movement of the translating shaft 152. As the transfer collar 174 translates, the translating shaft 152 translates distally and proximally.

The transfer collar 174 can include a lumen 180. The lumen 180 can be sized to receive a portion of the translating shaft 152 therein. The output shaft 124 and the translating shaft 152 can be coupled. In some embodiments, the output shaft 124 can include male threads and the translating shaft 152 can include female threads. In some embodiments, the output shaft 124 and the translating shaft 152 can be coupled in the lumen 180 of the transfer collar 174. As the transfer collar 174 translates, the output shaft 124 translates distally and proximally.

The translating shaft 152 can translate relative to the rotating shaft 148. The translating shaft 152 can translate relative to the transfer pin 150. The translating shaft 152 can include the slot 160. The slot 160 slides along the transfer pin 150 as the translating shaft 152 moves distally and proximally. The translating shaft 152 can translate longitudinally. The translating shaft 152 can translate longitudinally relative to the transfer pin 150. The translating shaft 152 can translate longitudinally relative to the rotating shaft 148. In some embodiments, the translating shaft 152 can translate the entire length of the slot 160. In some embodiments, the translating shaft 152 can translate only along a portion of the length of the slot 160. As the transfer collar 174 translates, the translating shaft 152 translates relative to the rotating shaft 148.

The translation of the filling auger 120 is the result of the rotation of the input shaft 140. The input shaft 140 rotates the spur gear 164 which rotates the secondary spur gear 166. The secondary spur gear 166 can be mounted on a stationary shaft 168. The secondary spur gear 166 rotates the axle 172 of the driving arm 170 between a distal most position of the axle 172 and a proximal most position of the axle 172. The driving arm 170 is translated distally when the axle 172 is at the distal most position. The driving arm 170 is translated proximally when the axle 172 is at the proximal most position. The driving arm 170 translates the transfer collar 174. The transfer collar 174 translates the translating shaft 152. The translating shaft 152 translates the output shaft 124. The output shaft 124 translates the shaft coupling 122 and the filling auger 120. As the output shaft 124 translates, the filling auger 120 translates, due to the coupling of these components by the shaft coupling 122.

The gear ratio between the spur gear 164 and the secondary spur gear 166 determines the timing between the proximal most position of the filling auger 120 and the distal most position of the filling auger 120. The spur gear 164 can have a 1" pitch diameter. The secondary spur gear 166 can have a 2" pitch diameter. The ratio or rotation of the spur gear 164 to the secondary spur gear 166 can be 2:1. Two rotations of the spur gear 164 can cause one rotation of the secondary spur gear 166. The spur gear ratio determines the rate of translation. The radial distance of the crank point or axle 172 on the secondary spur gear 166 determines the maximum speed of translation. The radial distance of the crank point or axle 172 on the secondary spur gear 166 determines the overall stroke distance from the most distal to most proximal positions.

Figure 11:
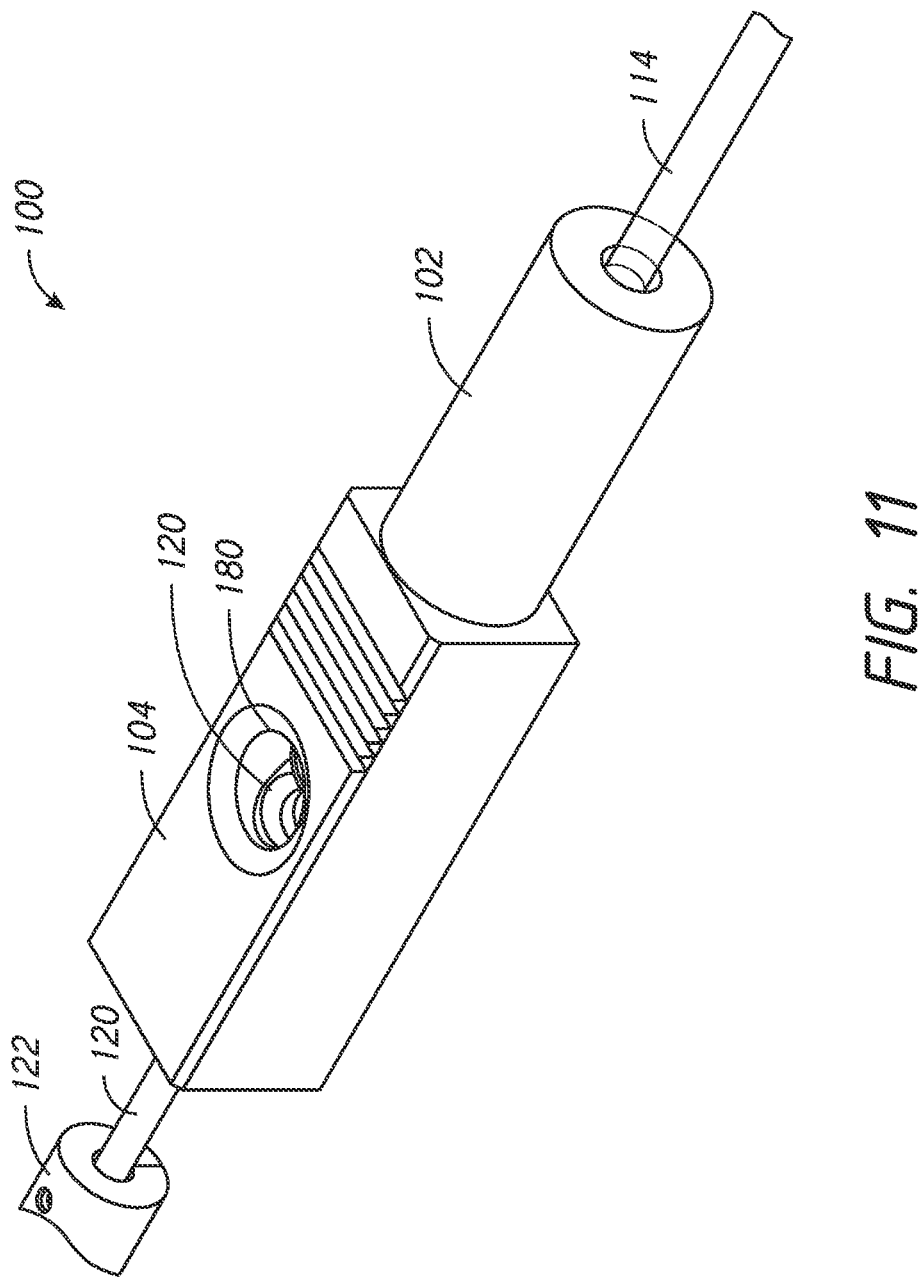
FIG. 11 is an enlarged perspective view of a portion of the filling assembly of FIG. 1.
Figure 12:
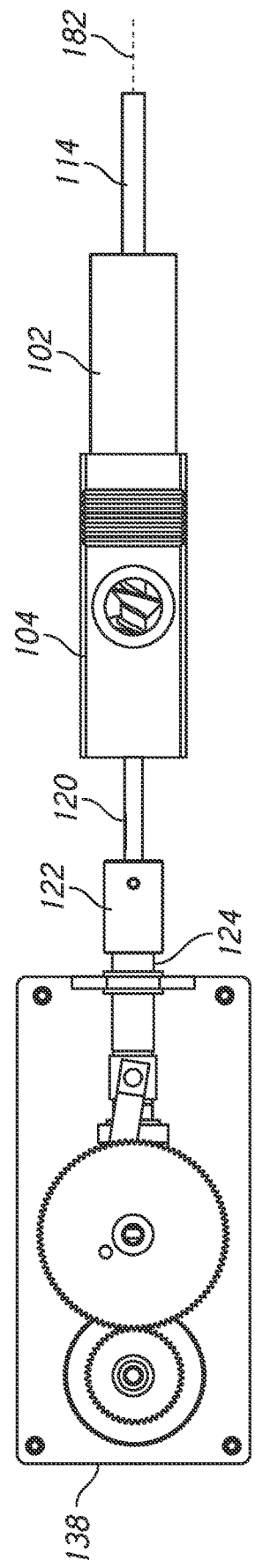
FIG. 12 is a top view of a portion of the filling assembly of FIG. 1.
Figure 13:
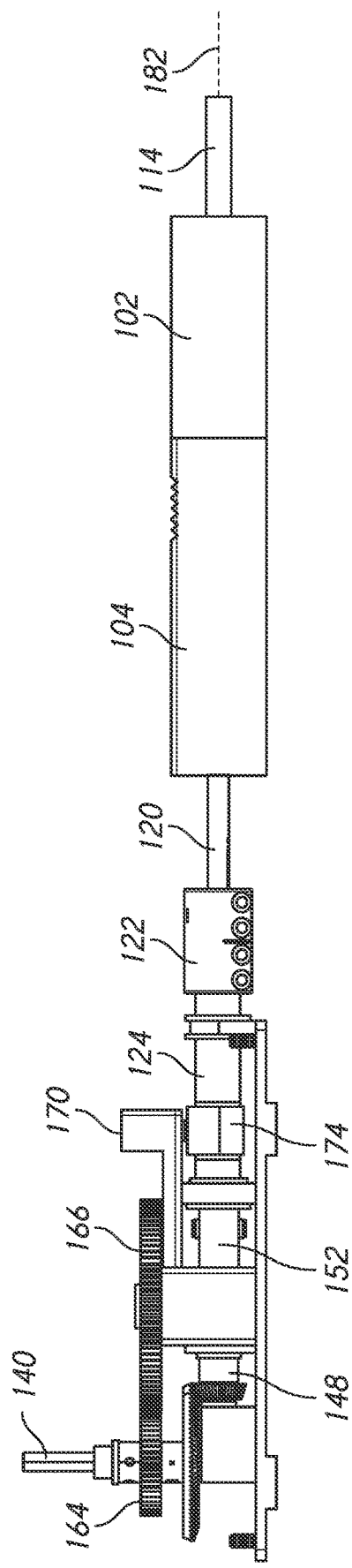
FIG. 13 is a side view of the portion of the filling assembly of FIG. 12.
Figure 14:
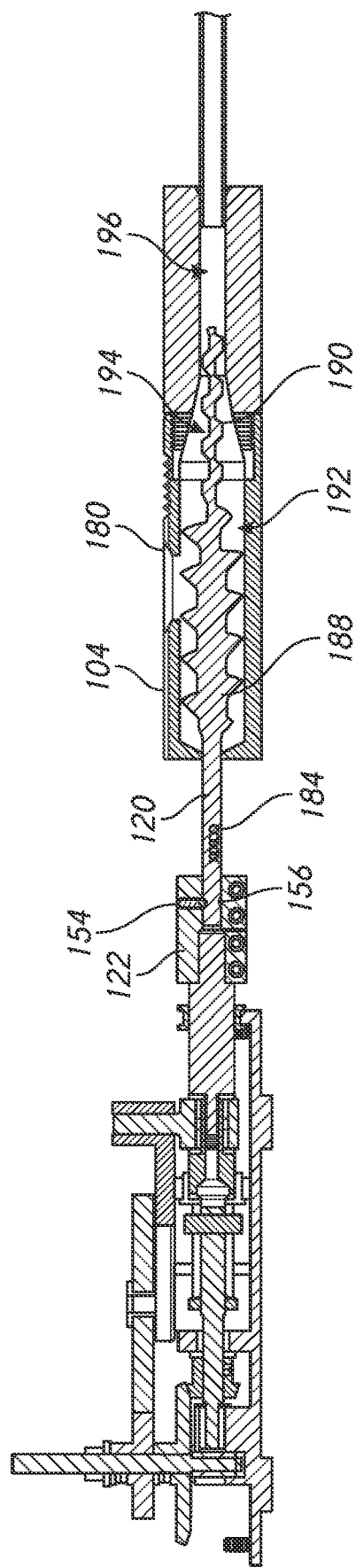
FIG. 14 is a cross-sectional side view of the portion of the filling assembly of FIG. 12.
Figure 15:
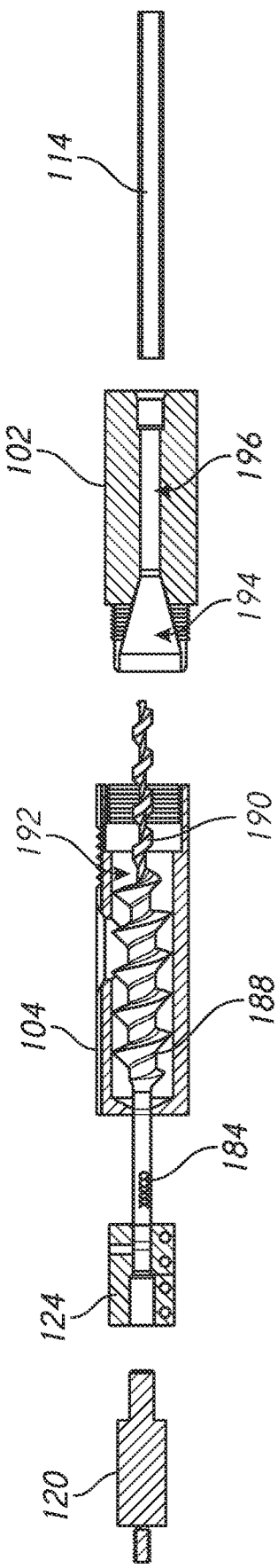
FIG. 15 is an exploded perspective view of a portion of the filling assembly of FIG. 1.

FIG. 11 illustrates an enlarged top perspective view of the filling assembly 100. FIG. 12 shows an enlarged top view of the filling assembly 100. FIG. 13 shows an enlarged side view of the filling assembly 100. FIG. 14 shows an enlarged cross-sectional view of the filling assembly 100. FIG. 15 is an exploded perspective view of the filling assembly 100.

FIGS. 11-15 illustrate the gearbox 130 with additional components of the filling assembly 100. The housing 134 shown in FIG. 4 is removed to show the internal components of the gearbox 130.

The shaft coupling 122 is coupled to the filling auger 120 and the output shaft 124. The rotational and translational forces of the gears of the gearbox 130 causes rotation and translation of the output shaft 124. The rotation and translation forces of the output shaft 124 causes rotation and translation of the filling auger 120. The filling auger 120 extends between the shaft coupling 122 and the receiving block 104. The filling auger 120 is at least partially disposed within the receiving block 104. The receiving block 104 is coupled to the barrel 102. The filling auger 120 is at least partially disposed within the barrel 102. In some embodiments, at least a tip of the filling auger 120 remains within the barrel 102 during use.

The receiving block 104 can include an opening 180. The opening 180 allows material to enter the receiving block 104. While the opening 180 is shown on the top side of the receiving block 104, the opening can be on any side of the receiving block 104. The funnel top 106 can be positioned over the opening 180. The material can be pushed into the opening 180 with the plunger 110. The material can flow into the opening 180 under the force of gravity. The filling auger 120 is viewable through the opening 180 in FIG. 11.

The tube 114 can be coupled to the barrel 102. The tube 114 can be a small diameter tube. The tube 114 can have a diameter of 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, or any range of the foregoing values. The tube 114 can be a thin walled tube. The tube 114 can include an open proximal end to allow the entry of material by the filling assembly 100. The tube 114 can include an open distal end. The tube 114 can include an open distal end to allow the venting of gases as material fills the tube 114.

The tube 114 can be loaded with material to be delivered to a surgical site. The tube 114 can be loaded with material manually. The tube 114 can be loaded with material by the rotation of the input shaft 140. The input shaft 140 can be rotated manually. The input shaft 140 can be rotated with a motor. The tube 114 can be loaded with material pre-operatively. The tube 114 can be loaded with material in a manufacturing setting. The tube 114 can be loaded with material by a third party vendor. The tube 114 can be loaded with material by a material manufacturer. The tube 114 can be loaded with material during a surgical procedure. The tube 114 can be loaded with material by a surgeon. The tube 114 can be loaded with material by hospital personnel. In some embodiments, the tube 114 is single use. In some embodiments, the tube 114 can be sterilized and reused.

The filling assembly 100 can have a longitudinal axis 182 extending between the proximal end 138 and the distal end 198. The longitudinal axis 182 can extend along the lumen of the tube 114. The longitudinal axis 182 can extend along the lumen of the barrel 102. The longitudinal axis 182 can extend along the lumen of the receiving block 104. The longitudinal axis 182 can extend along the axis of the filling auger 120. The longitudinal axis 182 can extend along the axis of the shaft coupling 122. The longitudinal axis 182 can extend along the axis of the output shaft 124. The longitudinal axis 182 can extend through the lumen 180 of the transfer collar 174. The longitudinal axis 182 can extend along the axis of the translating shaft 152. The longitudinal axis 182 can extend along the axis of the rotating shaft 148. The input shaft 140 can be perpendicular to the longitudinal axis 182. The axis of the opening 180 can be generally perpendicular to the longitudinal axis 182.

The tube 114 can be disposed near the distal end 198 of the filling assembly 100. The gearbox 130 can be disposed near the proximal end 138 of the filling assembly 100. While the components of the filling assembly 100 are shown aligned along the longitudinal axis 182, other configurations are contemplated. In some embodiments, the gearbox can be perpendicular to the longitudinal axis 182.

The rotation mechanism 142 extends generally along the longitudinal axis 182. The filling auger 120 rotates about the longitudinal axis 182. The filling auger 120 moves material along the longitudinal axis 182. The filling auger 120 acts as a screw conveyor to move material into the tube 114 along the longitudinal axis 182. The direction of the material into the tube 114 is proximal to distal as the filling auger 120 rotates.

The translation mechanism 162 extends generally parallel to the longitudinal axis 182. The spur gear 164 can be offset from the longitudinal axis 182. The secondary spur gear 166 can be offset from the longitudinal axis 182. The driving arm 170 can be offset from the longitudinal axis 182. The translation mechanism 162 acts upon the translating shaft 152 to translate the translating shaft 152. The translating shaft 152 translates proximally and distally along the longitudinal axis 182. The output shaft 124 is coupled to the translating shaft 152 such that translation of the translating shaft 152 causes translation of the output shaft 124. The output shaft 124 translates proximally and distally along the longitudinal axis 182. The filling auger 120 is coupled to the output shaft 124 such that translation of the output shaft 124 causes translation of the filling auger 120. The filling auger 120 translates along the longitudinal axis 182. The filling auger 120 moves material along the longitudinal axis 182 via a pneumatic pump action. The direction of the material into the tube 114 is proximal to distal as the filling auger 120 translates.

The filling auger 120 can have a shape to facilitate the movement of material. The filling auger 120 can include a shaft 184. The shaft 184 can be disposed within the shaft coupling 122. The shaft 184 can include the circumferential groove 156. The shaft 184 can extend between the shaft coupling 122 and the receiving block 104. The shaft 184 can have a constant cross-sectional dimension.

The filling auger 120 can include a helical screw blade or fighting. The filling auger 120 can act as screw conveyer upon rotation of the filling auger 120 as described herein. The fighting can be any shape to serve the function as a screw conveyer. The fighting can be sized to fit within the bores of the barrel 102 and the receiving block 104.

The filling auger 120 can include a larger diameter flight 188. The larger diameter flight 188 can form a helical thread. The larger diameter flight 188 can be a constant diameter. The larger diameter flight 188 can taper toward the proximal end. The larger diameter flight 188 can taper toward the distal end. The filling auger 120 can include a smaller diameter flight 190. The smaller diameter flight 190 can form a helical thread. The smaller diameter flight 190 can be a constant diameter. The smaller diameter flight 190 can taper toward the proximal end. The smaller diameter flight 190 can taper toward the distal end. The larger diameter flight 188 can be 1.5 times larger in diameter than the smaller diameter flight 190. The larger diameter flight 188 can be two or more times larger in diameter than the smaller diameter flight 190. The larger diameter flight 188 can have a diameter of 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, or any value or range of values between 6 mm and 20 mm, less than 6 mm, less than 7 mm, less than 8 mm, less than 9 mm, less than 10 mm, less than 11 mm, less than 12 mm, less than 13 mm, less than 14 mm, less than 15 mm, less than 16 mm, less than 17 mm, less than 18 mm, less than 19 mm, less than 20 mm, greater than 6 mm, greater than 7 mm, greater than 8 mm, greater than 9 mm, greater than 10 mm, greater than 11 mm, greater than 12 mm, greater than 13 mm, greater than 14 mm, greater than 15 mm, greater than 16 mm, greater than 17 mm, greater than 18 mm, greater than 19 mm, or greater than 20 mm.

The smaller diameter flight 190 can have a diameter of 1 mm, 2 mm, 3 mm, 4 mm, 5 mm, 6 mm, 7 mm, 8 mm, 9 mm, 10 mm, or any value or range of values between 1 mm and 10 mm, less than 1 mm, less than 2 mm, less than 3 mm, less than 4 mm, less than 5 mm, less than 6 mm, less than 7 mm, less than 8 mm, less than 9 mm, less than 10 mm, greater than 1 mm, greater than 2 mm, greater than 3 mm, greater than 4 mm, greater than 5 mm, greater than 6 mm, greater than 7 mm, greater than 8 mm, greater than 9 mm, or greater than 10 mm. The smaller diameter flight 190 can have the same or similar diameter as the diameter of the tube 114. The larger diameter flight 188 and the smaller diameter flight 190 can be left handed flights. The larger diameter flight 188 and the smaller diameter flight 190 can be configured to be rotated clockwise to move material forward.

The filling auger 120 can be partially disposed within the barrel 102 and the receiving block 104. The barrel 102 and the receiving block 104 can be coupled. In some embodiments, the barrel 102 can include male threads and the receiving block 104 can include female threads. In some embodiments, the barrel 102 and the receiving block 104 can be integrally or monolithically formed. The barrel 102 and the receiving block 104 can form a continuous cavity for the movement of material toward the tube 114.

The receiving block 104 can form a larger diameter bore 192. The shape of the larger diameter bore 192 can facilitate the movement of material. The larger diameter bore 192 can have a constant diameter. The opening 180 can extend into the larger diameter bore 192. In some embodiments, the diameter of the larger diameter bore 192 can be approximately equal to the diameter of the larger diameter flight 188. In some embodiments, the diameter of the larger diameter bore 192 is greater than the diameter of the larger diameter flight 188 of the filling auger 120.

The barrel 102 can include a cavity. The shape of the cavity can facilitate the movement of material. The barrel 102 can have a conical bore 194. The conical bore 194 can be uniformly tapered. The conical bore 194 can taper from a larger diameter to a smaller diameter. The larger diameter of the conical bore 194 of the barrel 102 can be approximately equal to the larger diameter bore 192 of the receiving block 104. The larger diameter bore 192 of the receiving block 104 and the conical bore 194 can be continuous. The angle of the conical bore 194 can facilitate the filling of material within the tube 114. The angle of the conical bore 194 can be more gradual than the angle of the larger diameter flight 188. The larger diameter flight 188 can push material into the conical bore 194 during the forward stroke. The angle of the conical bore can be approximately 45 degrees relative to the longitudinal axis 182. The angle of the conical bore can be less than 45 degrees relative to the longitudinal axis 182 such as 15 degrees, 20 degrees, 25 degrees, 30 degrees, 35 degrees, 40 degrees, or any range of the foregoing values.

The barrel 102 can have a smaller diameter bore 196. The smaller diameter of the conical bore 194 can be approximately equal to the smaller diameter bore 196. The smaller diameter of the conical bore 194 and the smaller diameter bore 196 can be continuous. The receiving block 104 can have the larger diameter bore 192. The barrel 102 can have the smaller diameter bore 196. The conical bore 194 of the barrel 102 can taper from the larger diameter to the smaller diameter. In some embodiments, the smaller diameter bore 196 of the barrel 102 can be approximately equal to the diameter of smaller diameter flight 190. In some embodiments, the smaller diameter bore 196 of the barrel 102 can be greater than the diameter of smaller diameter flight 190. The smaller diameter bore 196 can be equal to the diameter of the tube 114 to be filled. The smaller diameter bore 196 can be greater than the diameter of the tube 114 to be filled.

In some embodiments, the conical bore 194 can include grinder elements. In some embodiments, the conical bore 194 can include grooves. In some embodiments, the filling auger 120 can include grinder elements. In some embodiments, the filling auger 120 can include grooves. In some embodiments, the filling auger 120 between the larger diameter flight 188 and the smaller diameter flight 190 can include a conical section or tapering section. In some embodiments, the conical section or tapering section of the filling auger 120 can include grinder elements. In some embodiments, the conical section or tapering section of the filling auger 120 can include grooves. The grinder elements and/or grooves can be incorporated into any portion of the filling assembly 100. The grinder elements and/or grooves can facilitate the breaking down of oversized particulate in the material to facilitate entry of the material into the smaller diameter bore 196 of the barrel 102.

The larger diameter flight 188 of the filling auger 120 can be disposed within the larger diameter bore 192 of the receiving block 104. The larger diameter flight 188 of the filling auger 120 can rotate within the larger diameter bore 192 of the receiving block 104. The larger diameter flight 188 of the filling auger 120 can translate within the larger diameter bore 192 of the receiving block 104.

The smaller diameter flight 190 of the filling auger 120 can be disposed within the conical bore 194 of the barrel 102. The smaller diameter flight 190 of the filling auger 120 can rotate within the conical bore 194 of the barrel 102. The smaller diameter flight 190 of the filling auger 120 can translate within the conical bore 194 of the barrel 102.

The smaller diameter flight 190 of the filling auger 120 can be disposed within the smaller diameter bore 196 of the barrel 102. The smaller diameter flight 190 of the filling auger 120 can rotate within the smaller diameter bore 196 of the barrel 102. The smaller diameter flight 190 of the filling auger 120 can translate within the smaller diameter bore 196 of the barrel 102. In some embodiments, at least a portion of the smaller diameter flight 190 remains within the smaller diameter bore 196 of the barrel 102 during translation and rotation. The smaller diameter flight 190 can form a pneumatic pump with the smaller diameter bore 196 of the barrel 102. The smaller diameter flight 190 of the filling auger 120 can increase efficiency. The smaller diameter flight 190 of the filling auger 120 can facilitate the pneumatic pumping action. The smaller diameter flight 190 of the filling auger 120 remains sealed within the smaller diameter bore 196 of the barrel 102 during translation.

Figure 16:
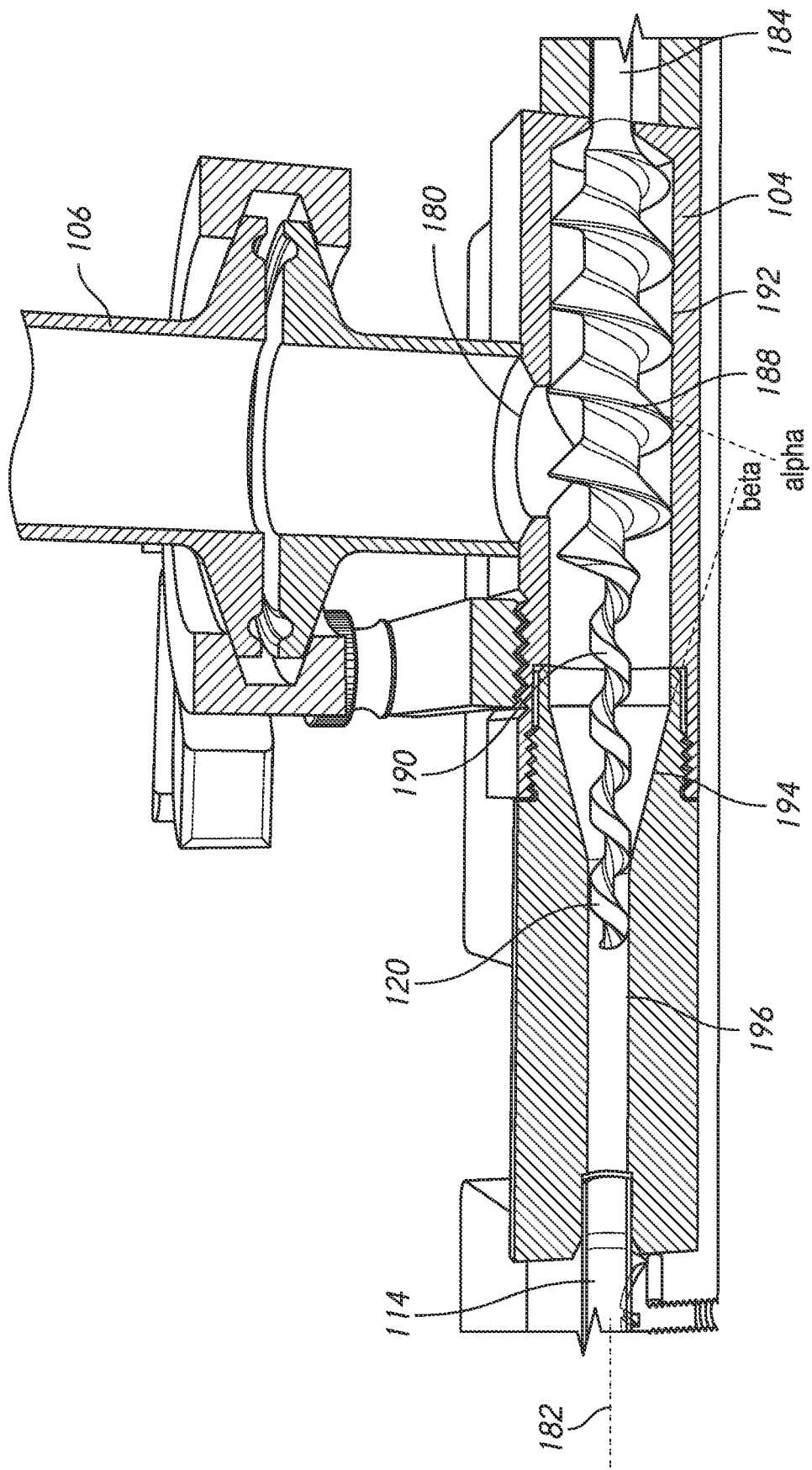
FIG. 16 is a cross-sectional side view of a filling auger of FIG. 1 in a first position.
Figure 17:
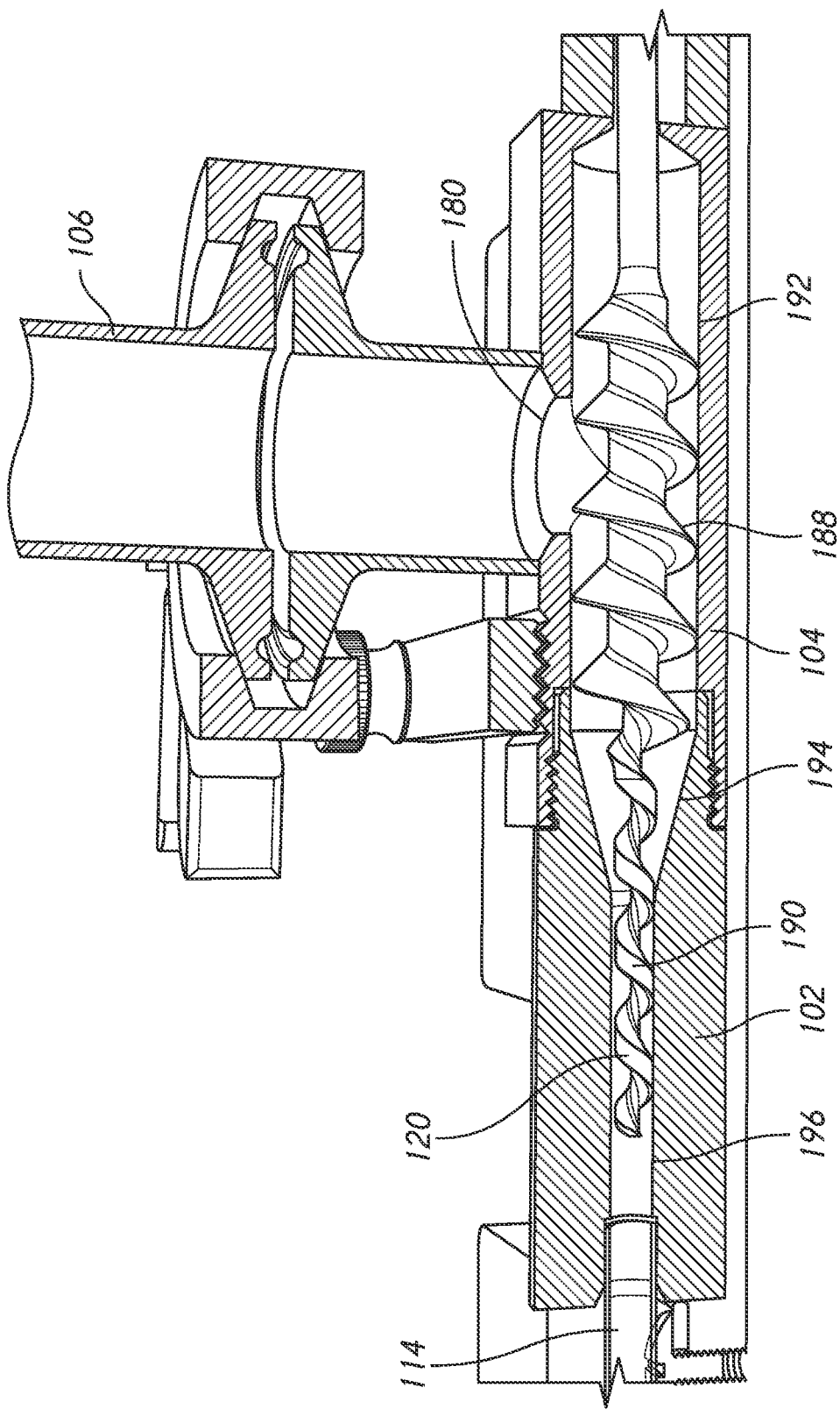
FIG. 17 is a cross-sectional side view of the filling auger of FIG. 16 in a second position.
Figure 18:
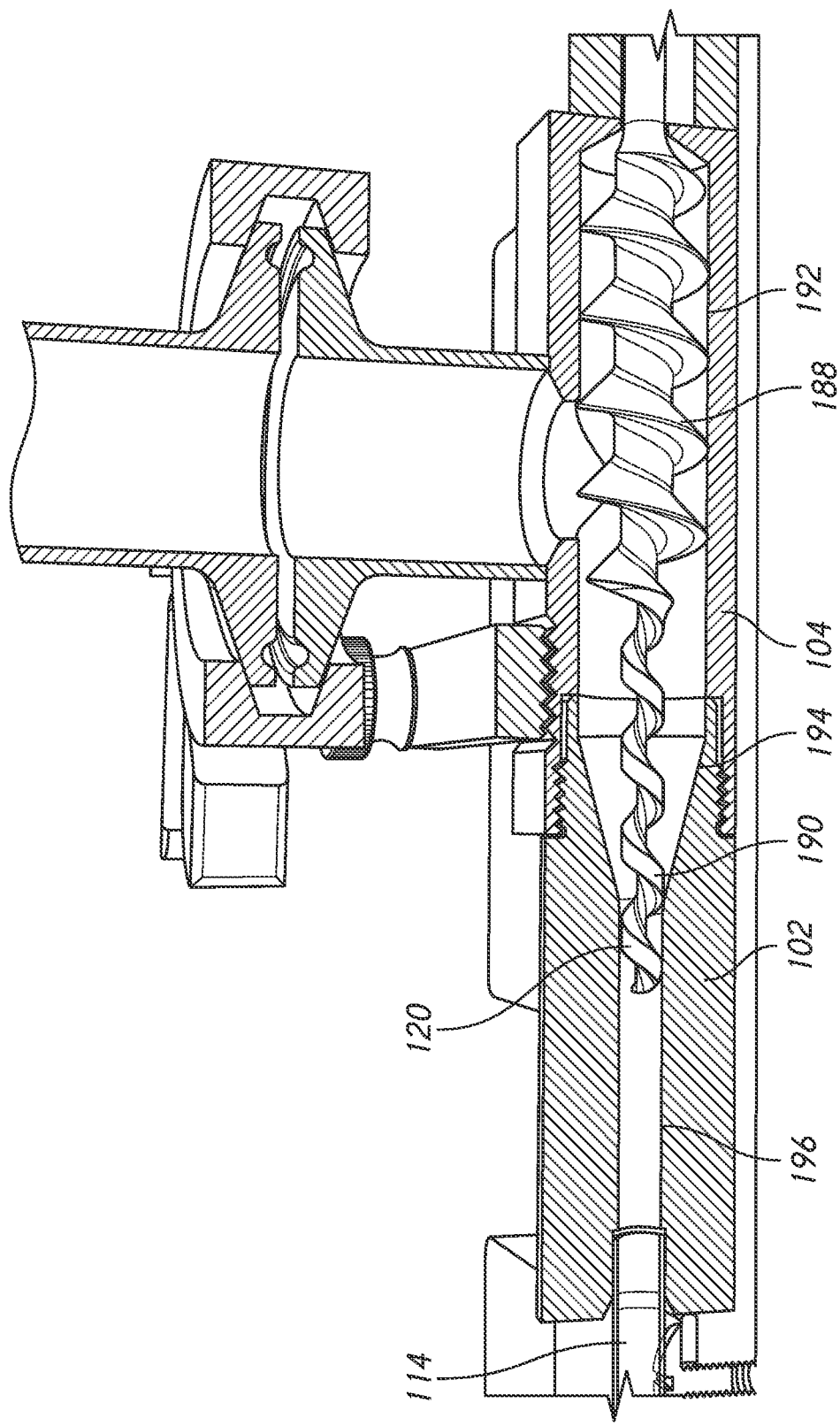
FIG. 18 is a cross-sectional side view of the filling auger of FIG. 16 in a third position.

FIG. 16 is a cross-sectional side view of the filling auger 120. The filling assembly 100 can move the filling auger 120 in a forward stroke and a backward stroke. FIG. 16 is a view of the filling auger 120 in the forward stroke in a first position. FIG. 17 is a cross-sectional side view of the filling auger 120 in the forward stroke in a second position. FIG. 18 is a cross-sectional side view of the filling auger 120 in the backward stroke in a third position. FIGS. 16-18 illustrate the filling auger 120 within the barrel 102 and the receiving block 104. A cross-sectional view is shown.

The filling auger 120 can be described as having a forward stroke and a backward stroke. Referring back to FIGS. 7 and 8, the input shaft 140 can be rotated causing the spur gear 164 and the secondary spur gear 166 to rotate. The axle 172 is coupled to the secondary spur gear 166. The filling auger 120 can have a forward stroke as the axle 172 moves from a proximal position to a distal position. The axle 172 is shown near the distal position in FIG. 7. The filling auger 120 can have a backward stroke as the axle 172 moves from a distal position to a proximal position. The filling auger 120 can have a forward stroke as the axle 172 moves toward the tube 114. The filling auger 120 can have a backward stroke as the axle 172 moves away from the tube 114. The secondary spur gear 166 moves the driving arm 170. The translational force imparted by the driving arm 170 is transmitted to the filling auger 120. In particular, the driving arm 170 can be coupled to the transfer collar 174. The transfer collar 174 can be coupled to the output shaft 124 which can be coupled to the filling auger 120. The filling auger 120 can have a forward stroke as the transfer collar 174 moves from a proximal position to a distal position. The transfer collar 174 is shown near the distal position in FIG. 8. The filling auger 120 can have a backward stroke as the transfer collar 174 moves from a distal position to a proximal position. The filling auger 120 can have a forward stroke as the transfer collar 174 moves toward the tube 114. The filling auger 120 can have a backward stroke as the transfer collar 174 moves away from the tube 114.

The filling auger 120 simultaneously rotates and translates. In some embodiments, the filling auger 120 simultaneously rotates clockwise and translates in a proximal or distal direction. In some embodiments, the filling auger 120 rotates in only one direction. In some embodiments, the filling auger 120 rotates in only one direction while translating proximally and distally. In some embodiments, the filling auger 120 continuously rotates in a single direction. In some embodiments, the filling auger 120 continuously translates proximally and distally.

FIG. 16 is a cross-sectional side view of a proximal position of the filling auger 120 during a forward stroke. The input shaft 140 can be rotated causing the bevel gear 144 and the secondary bevel gear 146 to rotate. This rotational force is transmitted to the filling auger 120. The filling auger 120 rotates in the direction dictated by the rotation of the input shaft 140, the bevel gear 144, and the secondary bevel gear 146. In some embodiments, the filling auger 120 rotates clockwise during the forward stroke.

The larger diameter flight 188 of the filling auger 120 can be disposed within the larger diameter bore 192 of the receiving block 104. Material can flow or be pushed from the funnel top 106 toward the opening 180. Material enters the receiving block 104 through the opening 180.

The smaller diameter flight 190 of the filling auger 120 can span from the larger diameter bore 192 of the receiving block 104 to the smaller diameter bore 196 of the barrel 102. The smaller diameter flight 190 of the filling auger 120 can be disposed within the larger diameter bore 192 of the receiving block 104. The smaller diameter flight 190 of the filling auger 120 can be disposed within the conical bore 194 of the barrel 102. The smaller diameter flight 190 of the filling auger 120 can be disposed within the smaller diameter bore 196 of the barrel 102. At least a portion of the filling auger 120 remains within the smaller diameter bore 196 of the barrel 102 in the proximal-most position of the filling auger 120.

The rotation of the filling auger 120 can move material in a distal direction. The rotation of the filling auger 120 can move material toward the tube 114. The rotation of the filling auger 120 can move material as the filling auger 120 acts as a screw conveyor. The translation of the filling auger 120 on the forward stroke can move material in a distal direction. The translation of the filling auger 120 can move material toward the tube 114. The translation of the filling auger 120 can move material as the filling auger 120 acts as a pneumatic pump.

FIG. 17 is a cross-sectional side view of a distal position of the filling auger 120 during a forward stroke from FIG. 16. The filling auger 120 continuously rotates in the direction dictated by the rotation of the input shaft 140, the bevel gear 144, and the secondary bevel gear 146 during the forward stroke. In some embodiments, the filling auger 120 rotates clockwise. The forward stroke is caused by the translation of the filling auger 120 from a proximal position to a distal position. The forward stroke is caused by the translation of the filling auger 120 toward the tube 114.

The larger diameter flight 188 of the filling auger 120 is translated distally within the larger diameter bore 192 of the receiving block 104 at the distal most point of the forward stroke. Material can continuously flow through the opening 180 and into the receiving block 104 during the forward stroke. Material fills the spaces between the flights of the filling auger 120 during the forward stroke.

In some embodiments, the smaller diameter flight 190 of the filling auger 120 can be disposed completely in the barrel 102 at the distal most point of the forward stroke. In some embodiments, the smaller diameter flight 190 of the filling auger 120 can be disposed only in the barrel 102 at the distal most point of the forward stroke. In some embodiments, the smaller diameter flight 190 of the filling auger 120 can be disposed partially in the barrel 102 at the distal most point of the forward stroke. The smaller diameter flight 190 of the filling auger 120 can be disposed within the conical bore 194 of the barrel 102. The smaller diameter flight 190 of the filling auger 120 can be disposed within the smaller diameter bore 196 of the barrel 102.

The rotation of the filling auger 120 can move material disposed in the spaces in a distal direction during the forward stroke. The rotation of the filling auger 120 can move material distally toward the tube 114 during the forward stroke. The translation of the filling auger 120 on the forward stroke can move material distally toward the tube 114 during the forward stroke.

FIG. 18 is a cross-sectional side view of a proximal position of the filling auger 120 during a backward stroke from FIG. 17. The filling auger 120 continuously rotates in the direction dictated by the rotation of the input shaft 140, the bevel gear 144, and the secondary bevel gear 146 during the backward stroke. The rotation of the filling auger 120 can be in the same direction for the forward stroke and backward stroke. The filling auger 120 can continuously rotate regardless of the translational position of the filling auger 120. In some embodiments, the filling auger 120 rotates clockwise during the backward stroke.

The backward stroke is caused by the translation of the filling auger 120 from a distal position to a proximal position. The backward stroke is caused by the translation of the filling auger 120 away from the tube 114. In some embodiments, the filling assembly can be timed so that the filling auger 120 does not pull back the material on the backward stroke. In some embodiments, the material sticks to the inner bores of the barrel 102 and the receiving block 104. The rotation and the translation of the filling auger 120 can be timed to always advance material toward the tube. The rotation and the translation of the filling auger 120 can be timed to advance material toward the tube during the forward stroke and to not intentionally retract material away from the tube during the backward stroke. The gear ratios of the gears in the gearbox 130 can be selected for timed movements.

The larger diameter flight 188 of the filling auger 120 is translated proximally within the larger diameter bore 192 of the receiving block 104 during the backward stroke. The smaller diameter flight 190 of the filling auger 120 is translated proximally within the smaller diameter bore 196 of the barrel 102 during the backward stroke. The smaller diameter flight 190 of the filling auger 120 can be disposed within the conical bore 194 of the barrel 102 during the backward stroke. The smaller diameter flight 190 of the filling auger 120 can be disposed within the smaller diameter bore 196 of the barrel 102 during the backward stroke. The forward and backward strokes can be continuously repeated until the tube 114 is filled.

The filling assembly 100 can include a mechanism for filling a tube 114 with material. In some embodiments, the filling assembly 100 can be powered by hand. The input shaft 140 can be rotated by the user. In some embodiments, the filling assembly 100 can be powered by motorized equipment. The input shaft 140 can be rotated by a motor. The filling assembly 100 combines the concepts of a mechanical screw conveyor with a pneumatic pump. The filling assembly 100 utilizes the filling auger 120 to fill slender tubes 114 with material, such as viscous biologic material. The filling assembly 100 can allow for continuous feeding of the material. The filling assembly 100 can fill the tube 114 with material while not compressing and/or not heating the material.

The filling assembly 100 can include the barrel 102 and the receiving block 104 which contain the filling auger 120. In some embodiments, the barrel 102 can disassemble from the receiving block 104. The barrel 102 can have an inner diameter similar to that of the tube 114 being filled. The barrel 102 can terminate at a lumen with a diameter and/or size which nests over the tube 114 being filled. The barrel 102 assembles with the receiving block 104. The receiving block 104 can have a larger inner diameter. The larger inner diameter of the receiving block 104 can facilitate feeding of material from the opening 180 exiting from the side and/or top of the receiving block 104. The filling auger 120 fits within the barrel 102 and the receiving block 104 when assembled. The filling auger 120 necks down from a large diameter fitting in the larger bore of the receiving block 104 down to the smaller diameter fitting in the smaller bore in the barrel 102. The filling auger 120 is dimensioned to allow for translation within the barrel 102 and the receiving block 104. The filling auger 120 is dimensioned to protrude into the smaller bore in the barrel 102 at all times. The shaft of the filling auger 120 protrudes from the rear end of the receiving block 104 at all times. The shaft of the filling auger 120 can be coupled to the gearbox 130 which causes the rotation and translation of the filling auger 120.

The barrel 102 can include a conical bore 194 extending between the larger bore 192 of the receiving block 104 and the smaller bore 196 of the barrel 102. The flights of the filling auger 120 can be angled at a steeper distal angle α (alpha) than an angle β (beta) of the conical bore 196 of the barrel 102 relative to the longitudinal axis 182. The angle α (alpha) of flights of the filling auger 120 can be angled relative to the longitudinal axis 182 such as 35 degrees, 40 degrees, 45 degrees, 50 degrees, 55 degrees, 60 degrees, 65 degrees, 70 degrees, 75 degrees, or any range of the foregoing values. The angle α (alpha) of flights of the filling auger 120 can be approximately 59 degrees. The angle β (beta) of the conical bore 194 of the barrel 102 can be angled relative to the longitudinal axis 182 such as 15 degrees, 20 degrees, 25 degrees, 30 degrees, 35 degrees, 40 degrees, 45 degrees, or any range of the foregoing values. The angle β (beta) of the conical bore 194 of the barrel 102 can be approximately 15 degrees. The flights of the filling auger 120 can be angled at a steeper distal angle α than the angle β of the conical portion 196 of the bore of the barrel 102 so as to allow material to more easily translate from the larger bore 192 down to the smaller diameter bore 196 of the barrel 102.

The gearbox 130 can couple to the shaft of the filling auger 120 protruding from the barrel 102 and the receiving block 104. The gearbox 130 converts input rotation into combined rotation and translation of the filling auger 120. The input shaft 140 powers a crank attached to the driving arm 170 which drives the output shaft 124 forwards and backwards. The input shaft 140 also powers the rotating shaft 148 which transfers torque to the output shaft 124. The transfer pin 150 and the slotted translating shaft 152 couples the rotating shaft 148 to the output shaft 124. This configuration of the transfer pin 150 and the slotted translating shaft 152 allows for translation of the output shaft 124. The gearbox 130 contains gears 144, 146, 164, 166 transmitting power to the translating and rotating assemblies whose ratios and crank distance to axle 172 are set such that the combined translation and rotation of the output shaft 124 (expressed as linear velocity/frequency of revolution or more simply translated distance/revolution) is at or lower than the pitch (length/rotation) of the auger flights of the filling auger 120.

The filling assembly 100 can be dimensioned to facilitate forward movement of the material. The larger bore 192 of the receiving block 104 can have a diameter of 10 mm, 11 mm, 12 mm, 13 mm, 14 mm, 15 mm, 16 mm, 17 mm, 18 mm, 19 mm, 20 mm, or any value or range of values between 10 mm and 20 mm, less than 10 mm, less than 11 mm, less than 12 mm, less than 13 mm, less than 14 mm, less than 15 mm, less than 16 mm, less than 17 mm, less than 18 mm, less than 19 mm, less than 20 mm, greater than 6 mm, greater than 7 mm, greater than 8 mm, greater than 9 mm, greater than 10 mm, greater than 11 mm, greater than 12 mm, greater than 13 mm, greater than 14 mm, or greater than 15 mm. In some embodiments, the diameter of the smaller bore 196 of the barrel 102 is approximately 15 mm (0.600 in). The smaller bore 196 of the barrel 102 can have an inner diameter of 3 mm, 4 mm, 5 mm, 6 mm, 7 mm, 8 mm, between 3 mm and 8 mm, between 4 mm and 6 mm, or any value or range of values between 3 mm and 10 mm, less than 3 mm, less than 4 mm, less than 5 mm, less than 6 mm, less than 7 mm, less than 8 mm, greater than 3 mm, greater than 4 mm, greater than 5 mm, greater than 6 mm, greater than 7 mm, or greater than 8 mm. In some embodiments, the diameter of the smaller bore 196 of the barrel 102 is approximately 5 mm (0.196 in).

The pitch of the auger flights of the filling auger 120 can be 5 mm/revolution (0.2 in/revolution), 7.5 mm/revolution (0.3 in/revolution), 10 mm/revolution (0.4 in/revolution), 12.5 mm/revolution (0.5 in/revolution), 15 mm/revolution (0.6 in/revolution), or any range of two of the foregoing values. In some embodiments, the pitch of the auger flights of the filling auger can be approximately 0.4 in/revolution (10 mm/revolution).

In some embodiments, the linear velocity of translation (LV) is equal to the crank radius times the driving speed divided by the gear ratio. The crank radius can be the distance of the axle 172 from the center of the secondary spur gear 166. The crank radius can be 7 mm (0.275 in), 8 mm (0.315 in), 9 mm (0.354 in), 10 mm (0.394 in), 11 mm (0.433 in), 12 mm (0.472 in), or any range of two of the foregoing values. In some embodiments, the crank radius can be approximately 0.350 in (9 mm). The gear ratio can be 2 between the spur gear 164 to the secondary spur gear 166. Two rotations of the spur gear 164 can cause one rotations of the secondary spur gear 166.

In some embodiments, the frequency of rotation (FR) is equal to the driving speed divided by the product of the gear ratio and 2π. The gear ratio can be ⅓ between the bevel gear 144 to the secondary bevel gear 146. One rotation of the bevel gear 144 can cause three rotations of the secondary bevel gear 146. The linear velocity of translation (LV) divided by the frequency of rotation (FR) can be approximately 0.367 in/rev. The pitch of the filling auger can be 0.4 in/revolution. The combined translation and rotation of the output shaft 124 (expressed as linear velocity divided by frequency of revolution) is at or lower than the pitch of the auger flights of the filling auger 120.

The pitch of the auger flights of the filling auger 120 is expressed as length or distance per rotation or revolution. The linear velocity of translation and the frequency of rotation is a result of using a geared system to setup the timing for the prescribed translation/revolution. The combined translation and rotation of the output shaft 124 (linear velocity divided by frequency of revolution) is directly comparable to translated distance/revolution of the filing auger 120. The comparison can be used to describe the filling assembly 100. In some embodiments, the combined translation and rotation of the output shaft 124 is less than the pitch of the auger flights of the filling auger 120.

The rotation of the filling auger 120 serves as a screw conveyor moving the material from the larger diameter of the receiving block 104 into the smaller diameter of the barrel 102. The length of the filling auger 120 within the smaller diameter lumen of the barrel 102 creates a pneumatic seal with the viscous material. Forward translation of the filling auger 120 pneumatically drives the material forward both within the barrel 102 and within the tube 114 being filled. The prescribed translation distance/revolution being equal to or lower than the auger pitch ensures material is always driven forward. The backwards translation of the filling auger 120 is not able to pull material back out as the flights are still rotating and serving as a forward screw conveyor.

The filling assembly 100 can include the filling base 112 which retains the receiving block 104, the barrel 102, the gearbox 130, and the tube 114 being filled. The support bracket 116 can have fill lines or indicia 118 indicating filling volume for hand operation.

The filling assembly 100 can have standard sanitary fittings which allow feeding of material by hand through the funnel top 106. Material may be fed into the receiving block 104 by any means including automated feeding, gravity, lip funnel and auger, etc. The filling assembly 100 can include the gearbox 130 connected to mechanical power such as electrical motor, power drill, stirrer, etc. Mechanical power can be toggled by hand or by foot pedal for hands free operation. The filling assembly 100 can be powered by a hand crank.

The tube 114 can be designed to place material at a surgical site. In some methods of use, the material is graft material. The graft material can be bone graft, including, but not limited to, autograft, allograft, xenograft, alloplastic graft, and/or a synthetic graft. In some methods, the bone graft can be inserted into the surgical site to promote fusion. In some methods, the bone graft can be inserted into the surgical site to restore the height between adjacent structures such as vertebral bodies. In some methods of use, the material is biologics. In some methods of use, the material is bone morphogenetic protein.

The tube 114 can be designed to be inserted into a surgical site. In some methods of use, the surgical site is the disc space between adjacent vertebrae. In some methods of use, the surgical site is between articular processes. In some methods of use, the surgical site is between spinous processes. In some methods of use, the surgical site is between transverse processes. In some methods of use, the surgical site is between adjacent bones. In some methods of use, the surgical site is between bone fragments. In some methods of use, the surgical site is within a joint. In some methods of use, the surgical site is within a joint capsule. In some methods of use, the surgical site is within a disc space. In some methods of use, the surgical site is any surgical site within the body of a patient.

Figure 19:
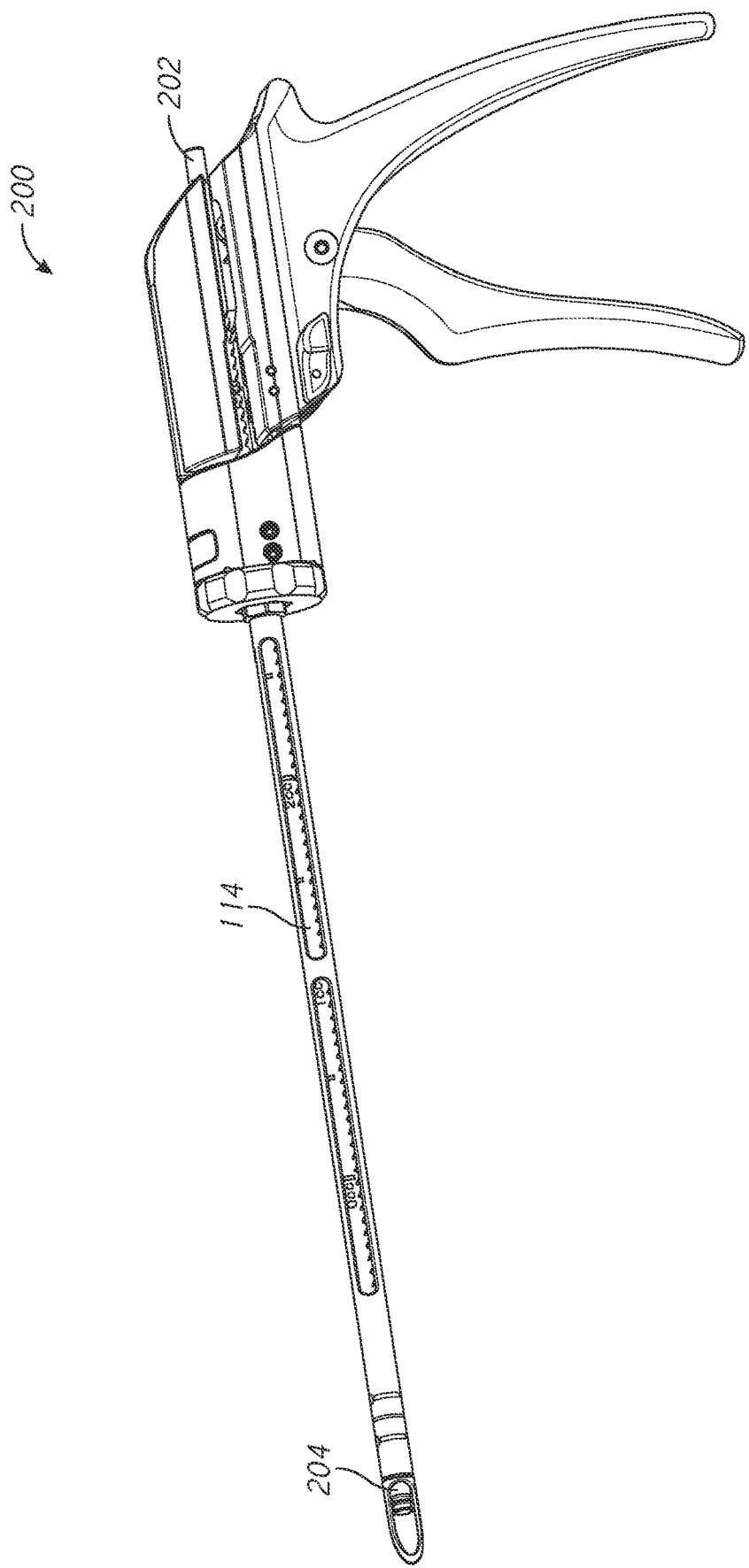
FIG. 19 illustrates a delivery device.
Figure 20:
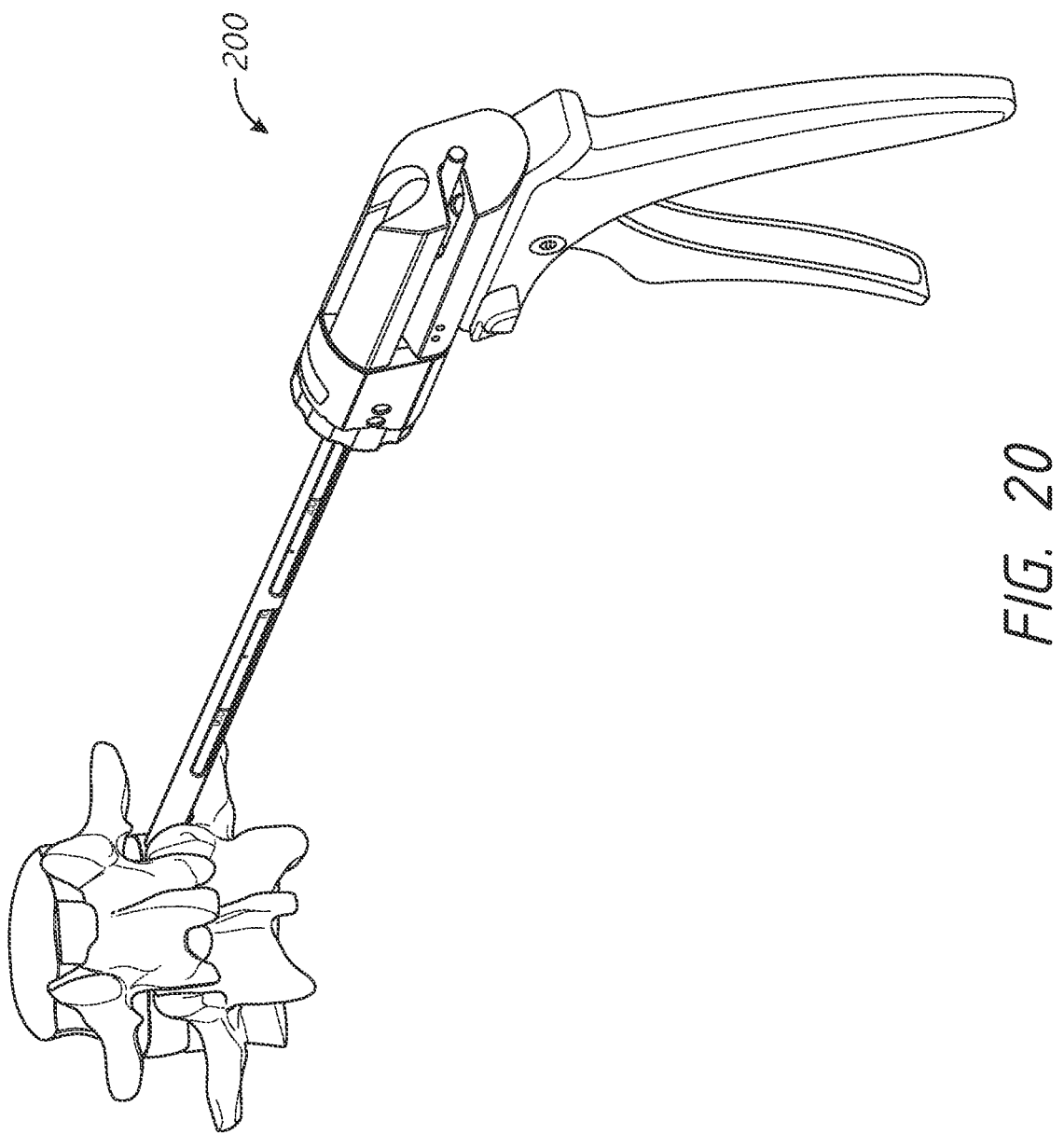
FIG. 20 illustrates the delivery device of FIG. 19 relative to the spine.

FIG. 19 illustrates a delivery device 200. FIG. 20 illustrates the delivery device 200 relative to the spine. The tube 114 can be used in combination with the delivery device 200. The delivery device 200 can include a ratchet rod 202. The tube 114 can be sized to receive the ratchet rod 202 within the lumen of the tube 114. FIG. 19 illustrates the tube 114 with the ratchet rod 202 disposed therein. The ratchet rod 202 can include a series of gears configured to be actuated by the delivery device 200. The ratchet rod 202 can include a plunger 204. The plunger 204 can push the contents of the tube 114 distally. The plunger can push the contents of the tube 114 toward an open end of the tube 114. The plunger 204 can be sized to scrape the inside of the tube 114 when the ratchet rod 202 is advanced. FIG. 19 shows the distal most position of the plunger 204. In some embodiments, the plunger 204 and the ratchet rod 202 are integrally formed. Examples of delivery devices can be found in U.S. Provisional Application 62/986,427 filed Mar. 6, 2020 and hereby incorporated by reference in its entirety. While delivery device 200 is illustrated, the tube 114 can be utilized with any delivery device.

In some embodiments, a kit is provided to the user. In some embodiments, the filling assembly 100 is provided in a kit. In some embodiments, one or more tubes 114 are provided in a kit. In some embodiments, one or more barrels 102 are provided in a kit. In some embodiments, the delivery device is provided in a kit. In some embodiments, the filling assembly 100 is reusable. In some embodiments, the tube 114 is reusable. In some methods of use, the tube 114 is disposable. In some embodiments, the barrel 102 is reusable. In some embodiments, the delivery device is reusable.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. For all the embodiments described above, the steps of the methods need not be performed sequentially. Thus, it is intended that the scope of the present invention herein disclosed should not be limited by the particular disclosed embodiments described above, but should be determined only by a fair reading of the claims that follow.

What is claimed is:

1. A filling assembly comprising:
an assembly configured to couple to a tube, wherein the assembly comprises a barrel and a receiving block; and
a filling auger;
wherein flights of the filling auger are configured to rotate and translate to fill the tube with material, wherein the filling auger is configured to have a forward stroke and a backward stroke relative to the assembly and the tube.

2. The filling assembly of claim 1, wherein the material comprises biologics, medicine, bone morphogenetic protein, a bone graft, autograft, allograft, xenograft, alloplastic graft, or a synthetic graft.

3. The filling assembly of claim 1, further comprising the tube, wherein the tube comprises a diameter to length ratio greater than 1:50 and a maximum diameter of 8 mm, wherein the tube is configured to deliver material to a surgical site.

4. The filling assembly of claim 1, wherein the barrel comprises a conical bore and a smaller diameter bore, wherein the receiving block comprises a larger diameter bore, wherein the barrel and the receiving block are configured to removably couple to form the assembly.

5. The filling assembly of claim 1, wherein the filling auger comprises a larger diameter flight and a smaller diameter flight.

6. The filling assembly of claim 1, wherein the assembly comprises a larger diameter bore, a conical bore, and a smaller diameter bore.

7. The filling assembly of claim 1, wherein the filling auger comprises a larger diameter flight configured to be disposed in a larger diameter bore of the assembly and a smaller diameter flight configured to be disposed in a smaller diameter bore of the assembly.

8. The filling assembly of claim 1, wherein the filling auger is configured to allow translation within the assembly while protruding into a smaller diameter bore of the assembly at all times during translation.

9. The filling assembly of claim 1, further comprising a gearbox coupled to the filling auger, wherein the gearbox converts input rotation into combined rotation and translation of the filling auger.

10. The filling assembly of claim 9, wherein the gearbox comprise a crank configured to translate the filling auger and gears configured to rotate the filling auger.

11. A method of filling a tube, the method comprising:
rotating and translating flights of a filling auger within an assembly comprising a barrel and a receiving block, wherein rotating and translating flights of the filling auger fills a tube with material, wherein the filling auger has a forward stroke and a backward stroke relative to the assembly and the tube; and
removing the tube from the assembly.

12. The method of claim 11, wherein the material comprises biologics, medicine, bone morphogenetic protein, a bone graft, autograft, allograft, xenograft, alloplastic graft, or a synthetic graft.

13. The method of claim 11, further comprising loading the tube into a delivery device.

14. The method of claim 13, further comprising delivering material to a surgical site with the delivery device.

15. The method of claim 11, wherein flights of the filling auger act as a screw conveyer moving material into the tube.

16. The method of claim 11, wherein flights of the filling auger act as a pneumatic pump moving material into the tube.

17. The method of claim 11, further comprising continuous feeding of material into the assembly while the tube is being filled.

18. The method of claim 11, wherein the tube is filled without compressing and/or heating the material.

19. The method of claim 11, wherein rotating and translating the filling auger comprises rotating and translating the filling auger with a motor.

20. The method of claim 11, wherein the filling auger comprises a larger diameter flight rotating and translating within a larger diameter bore of the assembly and a smaller diameter flight rotating and translating within a smaller diameter bore of the assembly.

* * * * *